(12) United States Patent
Muller et al.

(10) Patent No.: US 11,672,247 B2
(45) Date of Patent: *Jun. 13, 2023

(54) STABILIZATION OF THROMBOCYTES AT AMBIENT TEMPERATURES

(71) Applicant: Biomatrica, Inc., San Diego, CA (US)

(72) Inventors: Rolf Muller, Del Mar, CA (US); Joel Desharnais, La Mesa, CA (US); Steven P. Wilkinson, San Diego, CA (US); Victoria Arendt, San Diego, CA (US); Paul Diaz, Riverside, CA (US)

(73) Assignee: Biomatrica, Inc., San Diego, CA (US)

( * ) Notice: Subject to any disclaimer, the term of this patent is extended or adjusted under 35 U.S.C. 154(b) by 361 days.

This patent is subject to a terminal disclaimer.

(21) Appl. No.: 16/931,698

(22) Filed: Jul. 17, 2020

(65) Prior Publication Data

US 2020/0344999 A1 Nov. 5, 2020

Related U.S. Application Data

(63) Continuation of application No. 16/049,516, filed on Jul. 30, 2018, now Pat. No. 10,772,319, which is a continuation of application No. 15/316,677, filed as application No. PCT/US2015/034967 on Jun. 9, 2015, now Pat. No. 10,064,404.

(60) Provisional application No. 62/010,151, filed on Jun. 10, 2014.

(51) Int. Cl.
*A01N 1/02* (2006.01)
*A61K 35/19* (2015.01)

(52) U.S. Cl.
CPC .......... *A01N 1/0226* (2013.01); *A01N 1/021* (2013.01); *A61K 35/19* (2013.01)

(58) Field of Classification Search
None
See application file for complete search history.

(56) References Cited

U.S. PATENT DOCUMENTS

| | | |
|---|---|---|
| 3,673,158 A | 6/1972 | Reader et al. |
| 4,024,548 A | 5/1977 | Alonso et al. |
| 4,040,785 A | 8/1977 | Kim et al. |
| 4,127,502 A | 11/1978 | Li et al. |
| 4,185,964 A | 1/1980 | Lancaster |
| 4,257,958 A | 3/1981 | Powell |
| 4,264,560 A | 4/1981 | Natelson |
| 4,342,740 A | 8/1982 | Narra et al. |
| 4,451,569 A | 5/1984 | Kobayashi et al. |
| 4,473,552 A | 9/1984 | Jost |
| 4,683,195 A | 7/1987 | Mullis et al. |
| 4,683,202 A | 7/1987 | Mullis |
| 4,800,159 A | 1/1989 | Mullis et al. |
| 4,801,428 A | 1/1989 | Homolko et al. |
| 4,806,343 A | 2/1989 | Carpenter et al. |
| 4,842,758 A | 6/1989 | Crutzen |
| 4,889,818 A | 12/1989 | Gelfand et al. |
| 4,891,319 A | 1/1990 | Roser |
| 4,898,813 A | 2/1990 | Albarella et al. |
| 4,933,145 A | 6/1990 | Uchida et al. |
| 4,962,020 A | 10/1990 | Tabor et al. |
| 4,962,022 A | 10/1990 | Fleming et al. |
| 4,965,188 A | 10/1990 | Mullis et al. |
| 4,978,688 A | 12/1990 | Louderback |
| 5,039,704 A | 8/1991 | Smith et al. |
| 5,047,342 A | 9/1991 | Chatterjee |
| 5,071,648 A | 12/1991 | Rosenblatt |
| 5,078,997 A | 1/1992 | Hora et al. |
| 5,079,352 A | 1/1992 | Gelfand et al. |
| 5,089,407 A | 2/1992 | Baker et al. |
| 5,096,670 A | 3/1992 | Harris et al. |
| 5,096,744 A | 3/1992 | Takei et al. |
| 5,098,893 A | 3/1992 | Franks et al. |
| 5,147,803 A | 9/1992 | Enomoto |
| 5,198,353 A | 3/1993 | Hawkins et al. |
| 5,200,399 A | 4/1993 | Wettlaufer et al. |
| 5,240,843 A | 8/1993 | Gibson et al. |
| 5,242,792 A | 9/1993 | Rudolph et al. |
| 5,270,179 A | 12/1993 | Chatterjee |
| 5,290,765 A | 3/1994 | Wettlaufer et al. |
| 5,315,505 A | 5/1994 | Pratt et al. |

(Continued)

FOREIGN PATENT DOCUMENTS

| | | |
|---|---|---|
| CA | 1022441 A1 | 12/1977 |
| CA | 2467563 A1 | 5/2003 |

(Continued)

OTHER PUBLICATIONS

Allison et al., "Effects of Drying Methods and Additives on Structure and Function of Actin: Mechanisms of Dehydration-Induced Damage and Its Inhibition," Archives of Biochemistry and Biophysics 358(1):171-181, 1998.
Anchordoquy et al., "Frontiers in Clinical Research—Preservation of DNA," Cell Preservation Technology 5(4):180-188, 2007.
Ando et al., "PLGA Microspheres Containing Plasmid DNA: Preservation of Supercoiled DNA via Cryopreparatin and Carbohydrate Stabilization," Journ. Pharm. Sci., vol. 88, No. 1, pp. 126-130, 1999.
Anonymous, "Transmucosal polymeric molecular delivery systems," retrieved from http://www.antiagingresearch.com/hgh/transmucosal.php on Apr. 7, 2005, 2 pages.
"Antibiotics from Prokaryotes." https://www.boundless.com/microbiology/antimicrobial-drugs/commonly-used-antimicrobial-drugs/antibiotics-from-prokaryotes/, downloaded Aug. 1, 2014.

(Continued)

*Primary Examiner* — David W Berke-Schlessel
(74) *Attorney, Agent, or Firm* — Casimir Jones, S.C.; Peter J. Schlueter

(57) ABSTRACT

Provided herein are formulations and methods for the stabilization of one or more thrombocytes at ambient temperatures. Also provided are formulations and methods for the stabilization of one or more thrombocytes in an inactivated state in a blood sample at ambient temperatures. Further provided are articles of manufacture and kits and methods for substantially stable storage of one or more thrombocyte at ambient temperatures.

17 Claims, No Drawings

(56) References Cited

U.S. PATENT DOCUMENTS

| | | |
|---|---|---|
| 5,351,801 A | 10/1994 | Markin et al. |
| 5,374,553 A | 12/1994 | Gelfand et al. |
| 5,397,711 A | 3/1995 | Finckh |
| 5,403,706 A | 4/1995 | Wilk et al. |
| 5,409,818 A | 4/1995 | Davey et al. |
| 5,418,141 A | 5/1995 | Zweig et al. |
| 5,428,063 A | 6/1995 | Barak et al. |
| 5,436,149 A | 7/1995 | Barnes |
| 5,455,166 A | 10/1995 | Walker |
| 5,496,562 A | 3/1996 | Burgoyne |
| 5,498,523 A | 3/1996 | Tabor et al. |
| 5,512,462 A | 4/1996 | Cheng |
| 5,516,644 A | 5/1996 | Yamauchi et al. |
| 5,529,166 A | 6/1996 | Markin et al. |
| 5,541,290 A | 7/1996 | Harbeson et al. |
| 5,556,771 A | 9/1996 | Shen et al. |
| 5,593,824 A | 1/1997 | Treml et al. |
| 5,614,365 A | 3/1997 | Tabor et al. |
| 5,614,387 A | 3/1997 | Shen et al. |
| 5,684,045 A | 11/1997 | Smith et al. |
| 5,705,366 A | 1/1998 | Backus |
| 5,728,822 A | 3/1998 | Macfarlane |
| 5,741,462 A | 4/1998 | Nova et al. |
| 5,751,629 A | 5/1998 | Nova et al. |
| 5,763,157 A | 6/1998 | Treml et al. |
| 5,777,099 A | 7/1998 | Mehra |
| 5,777,303 A | 7/1998 | Berney |
| 5,779,983 A | 7/1998 | Dufresne et al. |
| 5,789,172 A | 8/1998 | Still et al. |
| 5,789,414 A | 8/1998 | Lapidot et al. |
| 5,798,035 A | 8/1998 | Kirk et al. |
| 5,814,502 A | 9/1998 | Hoeltke et al. |
| 5,827,874 A | 10/1998 | Meyer et al. |
| 5,834,254 A | 11/1998 | Shen et al. |
| 5,837,546 A | 11/1998 | Allen et al. |
| 5,856,102 A | 1/1999 | Bierke-Nelson et al. |
| 5,861,251 A | 1/1999 | Park et al. |
| 5,863,799 A | 1/1999 | Hengstenberg |
| 5,874,214 A | 2/1999 | Nova et al. |
| 5,876,992 A | 3/1999 | De et al. |
| 5,914,272 A | 6/1999 | Dufresne et al. |
| 5,918,273 A | 6/1999 | Horn |
| 5,939,259 A | 8/1999 | Harvey et al. |
| 5,945,515 A | 8/1999 | Chomczynski |
| 5,948,614 A | 9/1999 | Chatterjee |
| 5,955,448 A | 9/1999 | Colaco et al. |
| 5,985,214 A | 11/1999 | Stylli et al. |
| 5,991,729 A | 11/1999 | Barry et al. |
| 6,013,488 A | 1/2000 | Hayashizaki |
| 6,015,668 A | 1/2000 | Hughes et al. |
| 6,017,496 A | 1/2000 | Nova et al. |
| 6,025,129 A | 2/2000 | Nova et al. |
| 6,037,168 A | 3/2000 | Brown |
| 6,050,956 A | 4/2000 | Ikegami et al. |
| 6,057,117 A | 5/2000 | Harrison et al. |
| 6,057,159 A | 5/2000 | Lepre |
| 6,071,428 A | 6/2000 | Franks et al. |
| 6,090,925 A | 7/2000 | Woiszwillo et al. |
| 6,124,089 A | 9/2000 | Ryan |
| 6,127,155 A | 10/2000 | Gelfand et al. |
| 6,143,817 A | 11/2000 | Hallam et al. |
| 6,153,412 A | 11/2000 | Park et al. |
| 6,153,618 A | 11/2000 | Schultz et al. |
| 6,156,345 A | 12/2000 | Chudzik et al. |
| 6,166,117 A | 12/2000 | Miyazaki |
| 6,168,922 B1 | 1/2001 | Harvey et al. |
| 6,197,229 B1 | 3/2001 | Ando et al. |
| 6,204,375 B1 | 3/2001 | Lader |
| 6,221,599 B1 | 4/2001 | Hayashizaki |
| 6,242,235 B1 | 6/2001 | Shultz et al. |
| 6,251,599 B1 | 6/2001 | Chen et al. |
| 6,258,930 B1 | 7/2001 | Gauch et al. |
| 6,284,459 B1 | 9/2001 | Nova et al. |
| 6,294,203 B1 | 9/2001 | Burgoyne |
| 6,294,338 B1 | 9/2001 | Nunomura |
| 6,310,060 B1 | 10/2001 | Barrett et al. |
| 6,313,102 B1 | 11/2001 | Colaco et al. |
| 6,322,983 B1 | 11/2001 | Burgoyne |
| 6,323,039 B1 | 11/2001 | Dykens et al. |
| 6,329,139 B1 | 12/2001 | Nova et al. |
| 6,331,273 B1 | 12/2001 | Nova et al. |
| 6,352,854 B1 | 3/2002 | Nova et al. |
| 6,366,440 B1 | 4/2002 | Kung |
| 6,372,428 B1 | 4/2002 | Nova et al. |
| 6,372,437 B2 | 4/2002 | Hayashizaki |
| 6,380,858 B1 | 4/2002 | Yarin et al. |
| 6,416,714 B1 | 7/2002 | Nova et al. |
| 6,417,185 B1 | 7/2002 | Goff et al. |
| 6,426,210 B1 | 7/2002 | Franks et al. |
| 6,440,966 B1 | 8/2002 | Barrett et al. |
| 6,447,726 B1 | 9/2002 | Delucas et al. |
| 6,447,804 B1 | 9/2002 | Burgoyne |
| 6,448,245 B1 | 9/2002 | Depetrillo et al. |
| RE37,872 E | 10/2002 | Franks et al. |
| 6,458,556 B1 | 10/2002 | Hayashizaki |
| 6,465,231 B2 | 10/2002 | Harrison et al. |
| 6,475,716 B1 | 11/2002 | Seki |
| 6,489,344 B1 | 12/2002 | Nuss et al. |
| 6,503,411 B1 | 1/2003 | Franks et al. |
| 6,503,702 B1 | 1/2003 | Stewart |
| 6,528,309 B2 | 3/2003 | Levine |
| 6,534,483 B1 | 3/2003 | Bruno et al. |
| 6,535,129 B1 | 3/2003 | Petrick |
| 6,602,718 B1 | 8/2003 | Augello et al. |
| 6,608,632 B2 | 8/2003 | Daly et al. |
| 6,610,531 B1 | 8/2003 | Matecazun et al. |
| 6,617,170 B2 | 9/2003 | Augello et al. |
| 6,627,226 B2 | 9/2003 | Burgoyne et al. |
| 6,627,398 B1 | 9/2003 | Wilusz et al. |
| 6,638,945 B1 | 10/2003 | Gibson |
| 6,645,717 B1 | 11/2003 | Smith et al. |
| 6,649,406 B1 | 11/2003 | Williams et al. |
| 6,653,062 B1 | 11/2003 | Depablo et al. |
| 6,664,099 B1 | 12/2003 | Worrall |
| 6,667,167 B1 | 12/2003 | Sorensen et al. |
| 6,682,730 B2 | 1/2004 | Mickle et al. |
| 6,689,353 B1 | 2/2004 | Wang et al. |
| 6,696,028 B2 | 2/2004 | Bara |
| 6,746,841 B1 | 6/2004 | Fomovskaia et al. |
| 6,746,851 B1 | 6/2004 | Tseung et al. |
| 6,750,059 B1 | 6/2004 | Blakesley et al. |
| 6,776,959 B1 | 8/2004 | Helftenbein |
| 6,787,305 B1 | 9/2004 | Li et al. |
| 6,800,632 B2 | 10/2004 | Nuss et al. |
| 6,803,200 B2 | 10/2004 | Xia et al. |
| 6,821,479 B1 | 11/2004 | Smith et al. |
| 6,821,789 B2 | 11/2004 | Augello et al. |
| 6,852,833 B1 | 2/2005 | Machida et al. |
| 6,858,634 B2 | 2/2005 | Asrar et al. |
| 6,861,213 B2 | 3/2005 | Oelmuller et al. |
| 6,862,789 B1 | 3/2005 | Hering et al. |
| 6,872,357 B1 | 3/2005 | Bronshtein et al. |
| 6,896,894 B2 | 5/2005 | Brody et al. |
| 6,919,172 B2 | 7/2005 | Depablo et al. |
| 6,942,964 B1 | 9/2005 | Ward et al. |
| 6,949,544 B2 | 9/2005 | Bethiel et al. |
| 6,949,547 B2 | 9/2005 | Nuss et al. |
| 7,001,770 B1 | 2/2006 | Atencio et al. |
| 7,001,905 B2 | 2/2006 | Biwersi et al. |
| 7,011,825 B2 | 3/2006 | Yamazaki et al. |
| 7,037,918 B2 | 5/2006 | Nuss et al. |
| 7,045,519 B2 | 5/2006 | Nuss et al. |
| 7,049,065 B2 | 5/2006 | Hayashizaki |
| 7,083,106 B2 | 8/2006 | Albany |
| 7,098,033 B2 | 8/2006 | Chen et al. |
| 7,101,693 B2 | 9/2006 | Cicerone et al. |
| 7,129,242 B2 | 10/2006 | Yoshitaka et al. |
| 7,142,987 B2 | 11/2006 | Eggers |
| 7,150,980 B1 | 12/2006 | Lapidot et al. |
| 7,169,584 B2 | 1/2007 | Ward et al. |
| 7,169,816 B2 | 1/2007 | Barrett et al. |
| RE39,497 E | 2/2007 | Franks et al. |
| 7,172,999 B2 | 2/2007 | Mattern et al. |
| 7,258,873 B2 | 8/2007 | Truong-Le et al. |

(56) References Cited

U.S. PATENT DOCUMENTS

| | | |
|---|---|---|
| 7,270,953 B2 | 9/2007 | Hollaender et al. |
| 7,282,371 B2 | 10/2007 | Helftenbein |
| 7,326,418 B2 | 2/2008 | Franzoso et al. |
| 7,384,603 B2 | 6/2008 | Klein et al. |
| 7,425,557 B2 | 9/2008 | Nuss et al. |
| 7,476,754 B2 | 1/2009 | Herradon et al. |
| 7,521,460 B2 | 4/2009 | Langham et al. |
| 7,592,455 B2 | 9/2009 | Brookings et al. |
| 7,728,013 B2 | 6/2010 | Blatt et al. |
| 7,745,663 B2 | 6/2010 | Isshiki et al. |
| 7,795,256 B2 | 9/2010 | Alexander et al. |
| 7,803,839 B2 | 9/2010 | Aay et al. |
| 7,846,703 B2 | 12/2010 | Kobayashi et al. |
| 7,897,624 B2 | 3/2011 | Yan et al. |
| 7,919,294 B2 | 4/2011 | Franco et al. |
| 7,932,266 B2 | 4/2011 | Garcia et al. |
| 7,972,828 B2 | 7/2011 | Ward et al. |
| 8,143,271 B2 | 3/2012 | Ibrahim et al. |
| RE43,389 E | 5/2012 | Helftenbein |
| 8,178,555 B2 | 5/2012 | Chang et al. |
| 8,378,108 B2 | 2/2013 | Corkey et al. |
| 8,394,822 B2 | 3/2013 | Hutchings et al. |
| 8,440,665 B2 | 5/2013 | Corkey et al. |
| 8,492,427 B2 | 7/2013 | Gancia et al. |
| 8,519,125 B2 | 8/2013 | Whitney et al. |
| 8,530,480 B2 | 9/2013 | Kamenecka et al. |
| 8,598,360 B2 | 12/2013 | Corkey et al. |
| 8,642,584 B2 | 2/2014 | Aftab et al. |
| 8,664,244 B2 | 3/2014 | Chen |
| 8,827,874 B2 | 9/2014 | Nishimura |
| 8,900,856 B2 | 12/2014 | Muller-Cohn et al. |
| 9,078,426 B2 | 7/2015 | Muller-Cohn et al. |
| 9,376,709 B2 | 6/2016 | Whitney et al. |
| 2001/0038858 A1 | 11/2001 | Roser et al. |
| 2002/0039771 A1 | 4/2002 | Peters et al. |
| 2002/0055118 A1 | 5/2002 | Eym |
| 2002/0076819 A1 | 6/2002 | Bowman et al. |
| 2002/0081565 A1 | 6/2002 | Barnea et al. |
| 2002/0094533 A1 | 7/2002 | Hess et al. |
| 2002/0103086 A1 | 8/2002 | Asrar et al. |
| 2002/0182258 A1 | 12/2002 | Lunsford et al. |
| 2002/0197628 A1 | 12/2002 | Stewart |
| 2003/0022148 A1 | 1/2003 | Seki |
| 2003/0031697 A1 | 2/2003 | Chudzik et al. |
| 2003/0059468 A1 | 3/2003 | Mattern et al. |
| 2003/0091971 A1 | 5/2003 | Xia et al. |
| 2003/0119042 A1 | 6/2003 | Franco et al. |
| 2003/0129755 A1 | 7/2003 | Sadler et al. |
| 2003/0138805 A1 | 7/2003 | Loffert et al. |
| 2003/0157088 A1 | 8/2003 | Elliott et al. |
| 2003/0162284 A1 | 8/2003 | Dordick et al. |
| 2003/0163608 A1 | 8/2003 | Tiwary et al. |
| 2003/0165482 A1 | 9/2003 | Rolland et al. |
| 2003/0175232 A1 | 9/2003 | Elliott et al. |
| 2003/0199446 A1 | 10/2003 | Bunger et al. |
| 2003/0215369 A1 | 11/2003 | Eggers et al. |
| 2004/0014068 A1 | 1/2004 | Burgoyne |
| 2004/0058349 A1 | 3/2004 | Van et al. |
| 2004/0101966 A1 | 5/2004 | Davis et al. |
| 2004/0110267 A1 | 6/2004 | Sundar |
| 2004/0121420 A1 | 6/2004 | Smith |
| 2004/0121432 A1 | 6/2004 | Klein et al. |
| 2004/0142475 A1 | 7/2004 | Barman et al. |
| 2004/0208792 A1 | 10/2004 | Linton et al. |
| 2004/0228794 A1 | 11/2004 | Weller et al. |
| 2004/0241713 A1 | 12/2004 | Mirzabekov et al. |
| 2005/0026181 A1 | 2/2005 | Davis et al. |
| 2005/0053911 A1 | 3/2005 | Greener et al. |
| 2005/0084481 A1 | 4/2005 | Hand et al. |
| 2005/0086822 A1 | 4/2005 | Frisner et al. |
| 2005/0090009 A1 | 4/2005 | Cormier et al. |
| 2005/0112610 A1 | 5/2005 | Lee et al. |
| 2005/0186254 A1 | 8/2005 | Roser et al. |
| 2005/0196824 A1 | 9/2005 | Fisher et al. |
| 2005/0227269 A1 | 10/2005 | Lloyd et al. |
| 2005/0251501 A1 | 11/2005 | Phillips et al. |
| 2005/0276728 A1 | 12/2005 | Muller-Cohn et al. |
| 2006/0014177 A1 | 1/2006 | Hogan et al. |
| 2006/0099567 A1 | 5/2006 | Muller-Cohn et al. |
| 2006/0127415 A1 | 6/2006 | Mayeresse |
| 2006/0147944 A1 | 7/2006 | Chomczynski |
| 2006/0177855 A1 | 8/2006 | Utermohlen et al. |
| 2006/0183687 A1 | 8/2006 | Cory et al. |
| 2006/0193968 A1 | 8/2006 | Keogh et al. |
| 2006/0198891 A1 | 9/2006 | Ravenelle et al. |
| 2006/0210429 A1 | 9/2006 | Hunsley et al. |
| 2006/0293212 A1 | 12/2006 | Griese et al. |
| 2007/0020289 A1 | 1/2007 | Mattern et al. |
| 2007/0043216 A1 | 2/2007 | Bair et al. |
| 2007/0048726 A1 | 3/2007 | Baust et al. |
| 2007/0073039 A1 | 3/2007 | Chisari |
| 2007/0117173 A1 | 5/2007 | Levison et al. |
| 2007/0135528 A1 | 6/2007 | Butler et al. |
| 2007/0212760 A1 | 9/2007 | Lapidot et al. |
| 2007/0243178 A1 | 10/2007 | Ho et al. |
| 2008/0050737 A1 | 2/2008 | Arieli et al. |
| 2008/0064071 A1 | 3/2008 | Hogrefe et al. |
| 2008/0146790 A1 | 6/2008 | Grolz et al. |
| 2008/0176209 A1 | 7/2008 | Muller et al. |
| 2008/0187924 A1 | 8/2008 | Korfhage et al. |
| 2008/0227118 A1 | 9/2008 | Kohno et al. |
| 2008/0268514 A1 | 10/2008 | Muller et al. |
| 2008/0307117 A1 | 12/2008 | Muller-Cohn et al. |
| 2009/0010858 A1 | 1/2009 | Asano |
| 2009/0226545 A1 | 9/2009 | Blotsky et al. |
| 2009/0233283 A1 | 9/2009 | Rashtchian et al. |
| 2009/0239208 A1 | 9/2009 | Mayaudon et al. |
| 2009/0259023 A1 | 10/2009 | Su et al. |
| 2009/0291427 A1 | 11/2009 | Muller-Cohn et al. |
| 2009/0298132 A1 | 12/2009 | Muller-Cohn et al. |
| 2009/0312285 A1 | 12/2009 | Fischer et al. |
| 2010/0099150 A1 | 4/2010 | Fang et al. |
| 2010/0159528 A1 | 6/2010 | Liu et al. |
| 2010/0159529 A1 | 6/2010 | Metzler et al. |
| 2010/0178210 A1 | 7/2010 | Hogan et al. |
| 2010/0196904 A1 | 8/2010 | Arieli et al. |
| 2010/0261252 A1 | 10/2010 | Long et al. |
| 2010/0292447 A1 | 11/2010 | Pitner et al. |
| 2011/0014676 A1 | 1/2011 | Cowan et al. |
| 2011/0027862 A1 | 2/2011 | Bates et al. |
| 2011/0059490 A1 | 3/2011 | Lagunavicius et al. |
| 2011/0081363 A1 | 4/2011 | Whitney et al. |
| 2011/0111410 A1 | 5/2011 | Ryan et al. |
| 2012/0028933 A1 | 2/2012 | Baust et al. |
| 2012/0052572 A1 | 3/2012 | Whitney et al. |
| 2012/0100522 A1 | 4/2012 | Saghbini et al. |
| 2012/0142070 A1 | 6/2012 | Battrell et al. |
| 2012/0282634 A1 | 11/2012 | Hughes et al. |
| 2012/0295328 A1 | 11/2012 | Wyrich et al. |
| 2013/0066234 A1 | 3/2013 | Helftenbein |
| 2013/0209997 A1 | 8/2013 | Whitney et al. |
| 2014/0017712 A1 | 1/2014 | Shoji et al. |
| 2014/0065627 A1 | 3/2014 | Whitney et al. |
| 2014/0261474 A1 | 9/2014 | Gonda |
| 2015/0329849 A1 | 11/2015 | Whitney et al. |
| 2016/0135446 A1 | 5/2016 | Judy et al. |
| 2016/0338342 A1 | 11/2016 | Whitney et al. |
| 2018/0352806 A1* | 12/2018 | Desharnais .......... G01N 33/491 |

FOREIGN PATENT DOCUMENTS

| | | |
|---|---|---|
| CN | 101072506 | 11/2007 |
| CN | 102026619 A | 4/2011 |
| CN | 102846541 | 1/2013 |
| CN | 102947082 A | 2/2013 |
| CN | 103384496 | 11/2013 |
| CN | 105491883 A | 4/2016 |
| DE | 2424426 A1 | 3/1975 |
| DE | 19834816 A1 | 2/2000 |
| DE | 102008029734 A1 | 12/2009 |
| EP | 0448146 A1 | 9/1991 |
| EP | 0451924 A2 | 10/1991 |
| EP | 0493919 | 7/1992 |
| EP | 0329822 B1 | 6/1994 |

(56) References Cited

FOREIGN PATENT DOCUMENTS

| | | |
|---|---|---|
| EP | 0637750 A2 | 2/1995 |
| EP | 0706825 A1 | 4/1996 |
| EP | 0236069 B1 | 5/1997 |
| EP | 0774464 A2 | 5/1997 |
| EP | 0875292 A1 | 11/1998 |
| EP | 0915167 A1 | 5/1999 |
| EP | 1088060 A1 | 4/2001 |
| EP | 0833611 B1 | 8/2001 |
| EP | 0684315 B1 | 6/2002 |
| EP | 0822861 B1 | 11/2003 |
| EP | 1555033 A2 | 7/2005 |
| EP | 1082006 B1 | 2/2006 |
| EP | 0395736 B2 | 8/2006 |
| EP | 1736542 | 12/2006 |
| EP | 1758932 A2 | 3/2007 |
| EP | 1651712 B1 | 10/2007 |
| EP | 2934572 A2 | 10/2015 |
| EP | 3007556 A2 | 4/2016 |
| EP | 3154338 A1 | 4/2017 |
| EP | 3155091 A1 | 4/2017 |
| EP | 3155395 A1 | 4/2017 |
| GB | 2129551 A | 5/1984 |
| JP | S62502633 A | 10/1987 |
| JP | H08211065 A | 8/1996 |
| JP | H09-87183 | 3/1997 |
| JP | H09127106 A | 5/1997 |
| JP | 2000500327 A | 1/2000 |
| JP | 2001050872 A | 2/2001 |
| JP | 2009096766 A | 5/2009 |
| JP | 4421681 | 2/2010 |
| JP | 2012012303 | 1/2012 |
| JP | 2012072089 | 4/2012 |
| WO | WO-8607462 A1 | 12/1986 |
| WO | WO-8700196 A1 | 1/1987 |
| WO | WO-8701206 A1 | 2/1987 |
| WO | WO-8900012 A1 | 1/1989 |
| WO | WO-8906542 A1 | 7/1989 |
| WO | WO-9005182 A1 | 5/1990 |
| WO | WO-9114773 A2 | 10/1991 |
| WO | WO-9200091 A1 | 1/1992 |
| WO | WO-9206188 A2 | 4/1992 |
| WO | WO-9206200 A1 | 4/1992 |
| WO | WO 908349 | 5/1992 |
| WO | WO-9209300 A1 | 6/1992 |
| WO | WO-9211864 A1 | 7/1992 |
| WO | WO-9206188 A3 | 10/1992 |
| WO | WO-9501559 A2 | 1/1995 |
| WO | WO-9502046 A1 | 1/1995 |
| WO | WO-9510605 A1 | 4/1995 |
| WO | WO-9516198 A1 | 6/1995 |
| WO | WO-9610640 A1 | 4/1996 |
| WO | WO-9636436 A1 | 11/1996 |
| WO | WO-9700670 A1 | 1/1997 |
| WO | WO-9705248 A2 | 2/1997 |
| WO | WO 97/14785 | 4/1997 |
| WO | WO-9715394 A1 | 5/1997 |
| WO | WO-9815355 A2 | 4/1998 |
| WO | WO-9824543 A1 | 6/1998 |
| WO | WO 99/55346 | 11/1999 |
| WO | WO-9960849 A1 | 12/1999 |
| WO | WO-9967371 A1 | 12/1999 |
| WO | WO-0009746 A1 | 2/2000 |
| WO | WO-0014505 A1 | 3/2000 |
| WO | WO-0020117 A2 | 4/2000 |
| WO | WO-0062023 A1 | 10/2000 |
| WO | WO-0076664 A1 | 12/2000 |
| WO | WO-0137656 A2 | 5/2001 |
| WO | WO-0194016 A1 | 12/2001 |
| WO | WO-03020874 A2 | 3/2003 |
| WO | WO-03020924 A2 | 3/2003 |
| WO | WO-03056293 A2 | 7/2003 |
| WO | WO-03087335 A2 | 10/2003 |
| WO | WO-2004031363 A2 | 4/2004 |
| WO | WO-2004112476 A1 | 12/2004 |
| WO | WO-2005014704 A1 | 2/2005 |
| WO | WO-2005059178 A1 | 6/2005 |
| WO | WO-2005113147 A2 | 12/2005 |
| WO | WO-2005116081 A2 | 12/2005 |
| WO | WO-2006001499 A2 | 1/2006 |
| WO | WO 2006/128022 | 11/2006 |
| WO | WO 2007/016352 | 2/2007 |
| WO | WO-2007075253 A2 | 7/2007 |
| WO | WO-2007094581 A1 | 8/2007 |
| WO | WO-2008007463 A1 | 1/2008 |
| WO | WO-2008040126 A1 | 4/2008 |
| WO | WO-2008048228 A2 | 4/2008 |
| WO | WO-2008108549 A1 | 9/2008 |
| WO | WO-2009002568 A2 | 12/2008 |
| WO | WO-2009009210 A2 | 1/2009 |
| WO | WO-2009038853 A2 | 3/2009 |
| WO | WO-2010047592 A2 | 4/2010 |
| WO | WO-2010065924 A1 | 6/2010 |
| WO | WO-2010132508 A2 | 11/2010 |
| WO | WO-2010138522 A2 | 12/2010 |
| WO | WO 2011024199 | 3/2011 |
| WO | WO-2012018638 A2 | 2/2012 |
| WO | WO-2012018639 A2 | 2/2012 |
| WO | WO-2012170907 A2 | 12/2012 |
| WO | WO-2013077290 A1 | 5/2013 |
| WO | WO 2014049022 A1 | 4/2014 |
| WO | WO-2014100755 A2 | 6/2014 |
| WO | WO-2015002729 A2 | 1/2015 |
| WO | WO-2015191632 A1 | 12/2015 |
| WO | WO-2015191633 A1 | 12/2015 |
| WO | WO-2015191634 A1 | 12/2015 |

OTHER PUBLICATIONS

Arakawa et al., "Small molecule pharmacological chaperones: From thermodynamic stabilization to pharmaceutical drugs," Biochimica et Biophysica Acta 1764:1677-1687, 2006.

"Are supplements with amino acid chelated minerals better than those with other forms of minerals?" https://www.consumerlab.com/answers/Are+supplements+with+amino+acid+chelated+minerals+better+than+those+with+other+forms+of+minerals%3F/amino_acid_mineral_chelates/, downloaded Jul. 31, 2014, 1 page.

Asano, "Glycosidase inhibitors: update and perspectives on practical use," Glycobiology 13(10):93R-104R, 2003.

Balevicius et al., NMR and quantum chemistry study of mesoscopic effects in ionic liquids. J.Phys.Chem., 114:5365-5371, 2010.

Barnes, The fidelity of Taq polymerase catalyzing PCR is improved by an N-terminal deletion. Gene, 112:29-35, 1992.

Baskakov et al., "Forcing Thermodynamically Unfolded Proteins to Fold," The Journal of Biological Chemistry, 273(9):4831-4834, 1998.

"Borax: Friend or foe?" Momsaware.org webpage, http://www.momsaware.org/household-general/139-borax-friend-or-foe.html, downloaded Jul. 31, 2014, 1 page.

Boyd et al., "Stabilization Effect of Polyvinyl Alcohol on Horseradish Peroxidase, Glucose Oxidase, 13-Galactosidase and Alkaline Phosphatase," Biotechnology Techniques 10(9):693-698, 1996.

Braasch et al. Locked nucleic acid (LNA): fine-tuning the recognition of DNA and RNA. Chem Bio 8:1-7, 2001.

Branco et al., Preparation and characterization of new room temperature ionic liquids. Chem.Eur.J. 8:16, p. 3671-3677, 2002.

Buhler et al., "Viral Evolution in Response to the Broad-Based Retroviral Protease Inhibitor TL-3," Journal of Virology 75(19):9502-9508, 2001.

Calfon et al. IRE1 couples endoplasmic reticulum load to secretory capacity by processing the XBP-1 mRNA. Nature 415:92-96, 2002. (Abstract only).

Carninci et al., "Thermostabilization and thermoactivation of thermolabile enzymes by trehalose and its application for the synthesis of full length cDNA," Proc. Natl. Acad. Sci. USA 95:520-524, 1998.

Carpenter et al., "Stabilization of phosphofructokinase during air-drying with sugars and sugar/transition metal mixtures," Cryobiology 24(5):455-464, 1987. (Abstract).

(56) References Cited

OTHER PUBLICATIONS

Catalan et al., "Progress towards a generalized solvent polarity scale: The solvatochromism of 2-(dimethylamino)-7-nitrofluorene and its homomorph 2-fluoro-7-nitrofluorene", Liebigs Ann. 1995(2):241-252, 1995.

Catalan, Solvent effects based on pure solvent scales. In: Handbook of Solvents. Wypych G., ed. Toronto: ChemTec Publishing and New York: William Andrew Publishing. p. 583-616, 2001.

Cavalieri et al., "Chaperone-like activity of nanoparticles of hydrophobized poly(vinyl alcohol)," Soft Matter 3:718-724, 2007.

Chen et al., "Stabilization of Recombinant Human Keratinocyte Growth Factor by Osmolytes and Salts," Journal of Pharmaceutical Sciences, 85(4):419-426, 1996.

Cheng et al., "Chip PCR. II. Investigation of different PCR amplification systems in microfabricated silicon-glass chips," Nucleic Acids Res. 24:380-385, 1996.

Clement et al. Bioactive isomalabaricane triterpenoids from Rhabdastrella globostellata that stabile the binding of DNA polymerase beta to DNA. J. Nat. Prod., 69(3):373-6, 2006.

Clement et al., Following nature's lead: Generating compounds for stabilizing biomolecules. Biopreservation and Biobanking, 10(4):395-402, 2012.

Cohen et al., "Diffusion NMR Spectroscopy in Supramolecular and Combinatorial Chemistry: An Old Parameter—New Insights," Angew. Chem. Int. Ed., 44: 520-554, 2005.

Dagani, "Stir, Heat—But No Need to Dissolve," Chemical & Engineering News 81(5): 3 pages, 2003.

Dankwardt et al., "Stabilization of enzyme immunoassays for atrazine," Analytica Chimica Acta 362:35-45, 1998.

Daugherty et al., "Formulation and delivery issues for monoclonal antibody therapeutics," Advanced Drug Delivery Reviews 58:686-706, 2006.

De Sanctis et al., "Influence of Glycerol on the Structure and Redox Properties of Horse Heart Cytochrome c. A Circular Dichroism and Electrochemical Study," Journal of Protein Chemistry, 15(7):599-606, 1996.

Degim et al., "Controlled Delivery of Peptides and Proteins," Current Pharmaceutical Design 13:99-117, 2007.

Del Vigna de Almeida et al., Saliva composition and functions: A comprehensive review. The Journal of Contemporary Dental Practice, 9(3):72-80, 2008.

DePaz et al., "Effects of drying methods and additives on the structure, function, and storage stability of subtilisin: role of protein conformation and molecular mobility," Enzyme and Microbial Technology 31:765-774, 2002.

Di Tullio et al., "Molecular recognition by mass spectrometry," J. Mass Spectrom, 40(7):845-865, 2005.

DNA learning center, "Radiation can cause DNA mutations, 3D animation with narration." http://www.dnalc.org/view/15529-Radiation-can-cause-DNA-mutations-3D-animation-with-narration.html, downloaded Aug. 1, 2014.

Dong et al., "Biosynthesis of the Validamycins: Identification of Intermediates in the Biosynthesis of Validamycin A by *Streptomyces hygroscopicus* var. *limoneus*," J. Am. Chem. Soc. 123:2733-2742, 2001.

Dowell et al. Otitis media—principles of judicious use of antimicrobial agents. Pedatrics. 101 Suppl. 1: 165-171, 1998.

Dowell et al. Principles of judicious use of antimicrobial agents for pediatric upper respiratory tract infections. Pedatrics. 101 Suppl. 1:163-165, 1998.

Dyke et al., "Solvent-Free Functionalization of Carbon Nanotubes," J. Am. Chem. Soc. 125:1156-1157, 2003.

El-Bashiti, "Trehalose Metabolism In Wheat and Identification Of Trehalose Metabolizing Enzymes Under Abiotic Stress Conditions," Thesis, The Graduate School of Natural and Applied Sciences of the Middle East Technical University, Jul. 2003, 140 pages.

Ellison et al., Buffer capacities of human blood and plasma. Clinical Chemistry, 4(6):452-461, 1958.

Elzie et al., "The N-terminus of thrombospondin: the domain stands apart," The International Journal of Biochemistry & Cell Biology 36:1090-1101, 2004.

EP05778182.5 Office Action dated Apr. 28, 2010.
EP06848927.7 Office Action dated Jan. 20, 2009.
EP06848927.7 Office Action dated May 3, 2010.
EP06848927.7 Office Action dated Nov. 30, 2010.
EP08826300.9 Supplementary Search Report dated Oct. 26, 2010.
EP10775442.6 Extended European Search Report dated Jan. 21, 2014.
EP11815081.2 Extended European Search Report dated Nov. 5, 2013.
EP11815081.2 Office Action dated Jan. 15, 2015.
EP11815082.0 Extended European Search Report dated Nov. 5, 2013.
EP11815082.0 Office Action dated Jan. 15, 2015.
EP11815081.2 Communication dated Jan. 4, 2016.
EP11815082.0 Communication dated Jan. 4, 2016.
EP13865767.1 extended European Search Report dated Oct. 24, 2016.
EP14819510.0 extended European Search Report dated Feb. 7, 2017.
EP14819510.0 partial supplementary European Search Report dated Nov. 4, 2016.

Flaman et al., A rapid PCR fidelity assay. Nucleic Acids Research, 22(15): 3259-3260, 1994.

"Foods high in glycolic acid." http://www.ehow.com/list_5815634_foods-high-glycolic-acid.html, downloaded Jul. 31, 2014, 1 page.

Frye et al., "The kinetic basis for the stabilization of staphylococcal nuclease by xylose," Protein Science, 6:789-793, 1997.

Galinski et al., "1,4,5,6-Tetrahydro-2-methyl-4-pyrimidinecarboxylic acid. A novel cyclic amino acid from halophilic phototrophic bacteria of the genus *Ectothiorhodospira*," Eur. J. Biochem., 149:135-139, 1985.

Garcia de Castro et al., "Anhydrobiotic Engineering of Gram-Negative Bacteria," Applied and Environmental Microbiology 66(9):4142-4144, 2000.

Gerard et al., cDNA synthesis by moloney murine leukemia virus RNase H-minus reverse transcriptase possessing full DNA polymerase activity. Focus, 14(1): 91-93, 1992.

Godfrey, "Solvent selection via miscibility number," Chem. Technol. 2(6):359-363, 1972.

Goller et al., Protection of a model enzyme (lactate dehydrogenase) against heat, urea and freeze-thaw treatment by compatible solute additives, J. of Molecular Catalsys B: Enzymatic, 7(104):37-45,1999.

Gombotz et al., "Biodegradable Polymers for Protein and Peptide Drug Delivery," Bioconjugate Chem. 6:332-351, 1995.

Gowrishankar et al., Osmoregulation in Enterobacteriaceae: Role of proline/Betaine transport systems. Current Science, 57(5): 225-234, 1988.

Green DR, "Apoptosis. Death deceiver," Nature, 396(6712):629-30, 1998.

Green DR, "Apoptotic pathways: the roads to ruin," Cell, 94(6):695-69, 1998.

Green et al., "Mitochondria and apoptosis," Science, 281(5381):1309-12, 1998.

Harding et al., Perk Is Essential for Translational Regulation and Cell Survival during the Unfolded Protein Response. (2000) Mol Cell 5:897-904.

Haze et al., Mammalian Transcription Factor ATF6 Is Synthesized as a Transmembrane Protein and Activated by Proteolysis in Response to Endoplasmic Reticulum Stress. Mol Biol Cell 10(11):3787-3799, 1999.

Henke et al., Betaine improves the PCR amplification of GC-rich DNA sequences. Nucleic Acids Research, 25(19): 3957-3958, 1997.

Hewetson et al., Sucrose concentration in blood: A new method for assessment of gastric permeability in horses with gastric ulceration. J.Vet.Inter.Med., 20:388-394, 2006.

Hoffman, "Hydrogels for biomedical applications," Advanced Drug Delivery Reviews 43:3-12, 2002.

(56) References Cited

OTHER PUBLICATIONS

Holland et al., "Biological sample collection and processing for molecular epidemiological studies," Mutation Research 543:217-234, 2003.
Holland et al., "Molecular epidemiology biomarkers-Sample collection and processing considerations," Toxicology and Applied Pharmacology 206:261-268, 2005.
Houts et al., Reverse transcriptase from avian myeloblastosis virus. Journal of Virology, 29(2): 517-522, 1979.
Iyer et al., Enzyme stability and stabilization-Aqueous and nonaqueous environment, Process Biochemistry, 43:1019-1032, 2008.
Jin et al., Effect of mobile phase additives on resolution of some nucleic compounds in high performance liquid chromatography. Biotechnology and Bioprocess Engineering, 12:525-530, 2007.
Jones et al., "Long-term storage of DNA-free RNA for use in vaccine studies," BioTechniques 43(5):675-681, 2007.
Kaijalainen et al., "An alternative hot start technique for PCR in small volume using beads of wax-embedded reaction components dried in trehalose," Nucleic Acids Research 21(12):2959-2960, 1993.
Kameda et al., "New Cyclitols, Degradation of Validamycin A By Flavobacterium Saccharophilum," The Journal of Antibiotics 33(12):1573-1574, 1980.
Kaufman. Orchestrating the unfolded protein response in health and disease. J Clin Invest 110(10):389-1398, 2002.
Kilger and Paabo, Direct DNA sequence determination from total genomic DNA. Nucleic Acids Research, 25(10): 2032-2034, 1997.
Kim et al., Chemical Biology Investigation of Cell Death Pathways Activated by Endoplasmic Reticulum Stress Reveals Cytoprotective Modulators of ASK1S. J. Biol. Chem. 284(3):1593-1603, 2009.
Kirn-Safran et al., "Heparan Sulfate Proteoglycans: Coordinators of Multiple Signaling Pathways during Chondrogenesis," Birth Defects Research (Part C) 72:69-88, 2004.
Knapp et al., "Extrinsic protein stabilization by the naturally occurring osmolytes β-hydroxyectoine and betaine," Extremophiles, 3:191-198, 1999.
Knuesel et al., "Comparative studies of suidatrestin, a specific inhibitor of trehalases," Comparative Biochemistry and Physiology Part B 120:639-646,1998.
Komiyama et al., "Hydrolysis of DNA and RNA by lanthanide ions: mechanistic studies leading to new applications," Chem. Commun. :1443-1451, 1999.
Konishi et al., "Effects of Bay m 1099, an a-Glucosidase Inhibitor, on Starch Degradation in Germinating Mung Beans," Biosci. Biotechnol. Biochem. 62(1):142-144,1998.
Kotewicz et al., Isolation of closed Moloney murine leukemia virus reverse transcriptase lacking ribonuclease H activity. Nucleic Acid Research, 16(1):265, 1988.
Kravitz, Lactate: Not guilty as charged. IDEA Fitness Journal 2(6), 23-25, 2005 http://www.unm.edu/lkravitz/Article/%20folder/lactate.html, 3d paragraph, downloaded Jul. 31, 2014.
Kricka and Wilding, "Microchip PCR," Anal. Bioanal. Chem 377:820-825, 2003.
Kudo et al., A molecular chaperone inducer protects neurons from ER stress. Cell Death and Differentiation, 15:364-375, 2008.
Kumar et al., "The role of proline in the prevention of aggregation during protein folding in vitro," Biochemistry and Molecular Biology International, 46(3):509-517, 1998.
Langer. New methods of drug delivery. Science, New Series, vol. 249, No. 4976, pp. 1527-1533, 1990.
Langer, "Polymer-Controlled Drug Delivery Systems," Acc. Chem. Res. 26:537-542, 1993.
Lawyer et al., High-level expression, purification, and enzymatic characterization of full-length Thermus aquaticus DNA polymerase and a truncated form deficient in 5' to 3' exonuclease activity. PCR Methods and Applications, Cold Spring Harbor Laboratory Press, 2:275-287, 1993.
Lee et al., "Analysis of the S3 and S3' subsite specificities of feline immunodeficiency virus (FIV) protease: Development of a broad-based protease inhibitor efficacious against FIV, SW, and HIV in vitro and ex vivo," Proc. Natl. Acad. Sci. USA 95:939-944, 1998.
Lee et al., "Development of a New Type of Protease Inhibitors, Efficacious against FIV and HIV Variants," J. Am. Chem. Soc. 121:1145-1155, 1999.
Li et al., "Effect of Mobile Phase Additives on the Resolution of Four Bioactive Compounds by RP-HPLC", Int'l Journal of Molecular Sciences, 11(5):2229-2240, 2010.
Liao et al., "The effects of polyvinyl alcohol on the in vitro stability and delivery of spray-dried protein particles from surfactant-free HFA 134a-based pressurised metered dose inhalers," International Journal of Pharmaceutics 304:29-39, 2005.
Loo et al., Peptide and Protein Analysis by Electrospray Ionization—MassSpectrometry and Capillary Electrophoresis-Mass Spectrometry, Anal. Biochem., 179(2):404-412, 1989.
Lou et al., "Increased amplification efficiency of microchip-based PCR by dynamic surface passivation," Biotechniques, vol. 36, No. 2, pp. 248-252, 2004.
Lozano et al., Stabilization of x-Chymotrypsin by iconic liquids in transesterification reactions. Biotechnology and Bioengineerig, 75(5):563-569, 2001.
Luo et al., "Expression of a fusion protein of scFv-biotin mimetic peptide for immunoassay," J. Biotechnol. 65:225, 1998.
Malin et al., "Effect of Tetrahydropyrimidine Derivatives on Protein-Nucleic Acids Interaction," The Journal of Biological Chemistry, 274(11):6920-6929, 1999.
Manzanera et al., "Hydroxyectoine Is Superiorto Trehalose for Anhydrobiotic Engineering of Pseudomanas putida KT2440," Applied and Environmental Microbiology 68(9):4328-4333, 2002.
Manzanera et al., "Plastic Encapsulation of Stabilized *Escherichia coli* and Pseudomonas putida," Applied and Environmental Microbiology 70(5):3143-3145, 2004.
Marshall et al.," NXY-059, a Free Radical-Trapping Agent, Substantially Lessens the Functional Disability Resulting From Cerebral Ischemia in a Primate Species," Stroke, 32:190-198 (2001).
Mascellani et al., "Compatible solutes from hyperthermophiles improve the quality of DNA microarrays," BMC Biotechnology, 7(82):1-6, 2007.
Mitchell et al., "Dispersion of Functionalized Carbon Nanotubes in Polystyrene," Macromolecules 35:8825-8830, 2002.
Mizuguchi et al., Characterization and application to hot start PCR of neutralizing momoclonal antibodies against KOD DNA polymerase. J. Biochem., 126:762-768, 1999.
Mohr, "Reversible chemical reactions as the basis for optical sensors used to detect amines, alcohols and humidity," J. Mater. Chem., 9:2259-2264, 1999.
Mori K, Tripartite Management Mini review of Unfolded Proteins in the Endoplasmic Reticulum. Cell 101 (5):451-454, 2000.
Natale et al., Sensitivity of Bovine Blastocyst Gene Expression Patterns to Culture Environments Assessed by Differential Display RT-PCR. Reproduction, 122 (5): 687-693, 2001.
New England Biolabs 1993/1994, 4 pages.
Nielsen et al., Peptide nucleis acid (PNA). A DNA mimic with a peptide backbone. Bioconjugate Chemistry, 5:3-7, 1994.
O'Brien et al. Acute sinusitis—principles of judicious use of antimicrobial agents. Pedatrics. 101 Suppl. 1: 174-177, 1998.
O'Brien et al. Cough illness/bronchitis—principles of judicious use of antimicrobial agents. Pedatrics. 101 Suppl. 1: 178-181, 1998.
Okada et al. Distinct roles of activating transcription factor 6 (ATF6) and double-stranded RNA-activated protein kinase-like endoplasmic reticulum kinase (PERK) in transcription during the mammalian unfolded protein response. Biochem J 366(Pt 2):585-594, 2002.
Soltis and Skalka, The alpha and beta chains of avian retrovirus reverse transcriptase independently expressed in *Escherichia coli*: Characterization of enzymatic activities. Proc. Nat. Acad. Sci. USA, 85:3372-3376, 1968.
Ortega et al., "New functional roles for non-collagenous domains of basement membrane collagens," Journal of Cell Science 115:4201-4214, 2002.
Parsegian et al., "Macromolecules and Water: Probing with Osmotic Stress," Methods in Enzymology, 259:43-94, 1995.

(56) References Cited

OTHER PUBLICATIONS

Passot et al., "Physical characterization of formulations for the development of two stable freeze-dried proteins during both dried and liquid storage," European Journal of Pharmaceutics and Biopharmaceutics 60:335-348, 2005.
Pavlov et al., "The Role of ECM Molecules in Activity-Dependent Synaptic Development and Plasticity," Birth Defects Research (Part C) 72:12-24, 2004.
PCT/US2013/077290 International Preliminary Report on Patentability dated Jul. 2, 2015.
PCT/US2013/077290 International Search Report and Written Opinion dated Jun. 23, 2014.
PCT/US2014/042396 International Preliminary Report on Patentability dated Dec. 23, 2015.
PCT/US2015/034967 International Search Report and Written Opinion dated Sep. 16, 2015.
PCT/US2015/034968 International Search Report and Written Opinion dated Sep. 16, 2015.
PCT/US2015/034969 International Preliminary Reporton Patentability dated Dec. 22, 2016.
PCT/US2015/034969 International Search Report and Written Opinion dated Sep. 15, 2015.
PCT/US2016/065200 International Search Report and Written Opinion dated Feb. 16, 2017.
PCT/US2016/065198 International Search Report and Written Opinion dated Mar. 13, 2017.
PCT/US2005/012084 International Preliminary Report on Patentability dated Oct. 11, 2006.
PCT/US2006/45661 International Preliminary Report on Patentability dated Jun. 30, 2008.
PCT/US2006/45661 International Search Report and Written Opinion dated Nov. 13, 2007.
PCT/US2008/061332 International Preliminary Report on Patentability dated Oct. 27, 2009.
PCT/US2008/061332 International Search Report and Written Opinion dated Jul. 29, 2009.
PCT/US2008/068628 International Preliminary Report on Patentability dated Jan. 5, 2010.
PCT/US2008/068628 International Search Report and Written Opinion dated Aug. 27, 2009.
PCT/US2010/34454 International Preliminary Report on Patentability dated Nov. 15, 2011.
PCT/US2010/34454 International Search Report and Written Opinion dated Jan. 20, 2011.
PCT/US2011/045404 International Preliminary Report on Patentability dated Jan. 29, 2013.
PCT/US2011/045404 International Search Report and Written Opinion dated Mar. 27, 2012.
PCT/US2011/045405 International Preliminary Report on Patentability dated Jan. 29, 2013.
PCT/US2011/045405 International Search Report and Written Opinion dated Mar. 26, 2012.
PCT/US2005/012084 International Search Report dated Feb. 7, 2006.
PCT/US2014/042396 Written Opinion dated Mar. 13, 2015.
PCT/US2014/041396 International Search Report dated Mar. 13, 2015.
Peters et al., Sensitivity of human, murine, and rat cells to 5-Fluorouracil and 5'-Deoxy-5-fluorouridine in relation to drug-metabolizing enzymes Cancer Research, 46:20-28, 1986.
Pickering, LK, Ed. Red Book: Report of the Committee on Infectious Diseases, 26th edition. Elk Grove Village, IL, pp. 695-697, 2003.
Prestrelski et al., "Dehydration induced Conformational Transitions in Proteins and Their Inhibition by Stabilizers," Biophysical Journal 65:661-671, 1993.
Qu et al., Ambient stable quantitative PCR reagents for the detection of Yersinia pestis. PLoS Neglected Tropical Diseases, 4(3):e629, 2010.

Roberts, "Organic compatible solutes of halotolerant and halophilic microorganisms," Saline Systems, 1(5):1-30, 2005.
Roche. "PCR Reaction Components." Downloaded from the internet (http://www.roche-appliedscience.com/sis/amplification/pcr_amplification_050300.html; Downloaded on Dec. 13, 2012, 4 pages.
Ron and Walter, Signal integration in the endoplasmic reticulum unfolded protein response. Nat Rev Mol Cell Biol 8:519-529, 2007 (Abstract only).
Rosenstein et al. The common cold—principles of judicious use of antimicrobial agents. Pediatrics. 101 Suppl. 1: 181-184., 1998.
Sadeghi et al., Effect of alkyl chain length and temperature on the thermodynamic properties of ionic liquids 1-alkyl-3-methylimidazolium bromide in aqueous and non-aqueous solutions At different temperatures. J.Chem.Thermodynamics, 41:273-289, 2009.
Saiki et al. Primer-Directed Enzymatic Amplification of DNA with a Thermostable DNA Polymerase. Science 239:487-491, 1988.
Sauer et al., "Bacterial Milking: A Novel Bioprocess for Production of Compatible Solutes," Biotechnology and Bioengineering, 57(3):306-313, 1998.
Sawicki, "Foods high in Glutathione." http://www.ehow.com/list_6900955_foods-high-glutathione.html, downloaded Jul. 31, 2014, 1 page.
Schnoor, et al. Characterization of the synthetic compatible solute homoectoine as a potent PCR enhancer. Biochem and Biophys. Res. Comm, 322:867-872, 2004.
Schwartz et al. Pharyngitis—principles of judicious use of antimicrobial agents. Pedatrics. 101 Suppl. 1: 171-174, 1998.
Schyma, "Erfahrungen mit der PVAL-Methode in der rechtsmedizinischen Praxis," Arch. Kriminol. /97(1-2):41-46, 1996.
Schyma et al., "DNA-PCR Analysis of Bloodstains Samples by the Polyvinyl-Alcohol Method," Journal of Forensic Sciences 44(1):95-99, 1999.
Schyma et al., "The Accelerated Polyvinyl-Alcohol Method for GSR Collection-PVAL 2.0," Journal of Forensic Sciences 45(6):1303-1306, 2000.
Scouten, "A survey of enzyme coupling techniques," Methods in Enzymology, 135:30-65, 1987.
Sigma Catalog. St. Louis:Sigma-Aldrich. p. 1987, 1998.
Sirieix-Plenet et al., "Behaviour of a binary solvent mixture constituted by an amphiphilic ionic liquid, 1-decy1-3-methylimidazolium bromide and water Potentiometric and conductimetric studies," Talanta 63(4):979-986, Jul. 8, 2004.
Slita et al., "DNA-polycation complexes Effect of polycation structure on physico-chemical and biological properties," Journal of Biotechnology, 127:679-693, 2007.
Smith et al., "Optimal Storage Conditions for Highly Dilute DNA Sampled: A Role for Trehalose as a Preserving Agent," Journal of Forensic Science 50(5):1-8, 2005.
Sola-Penna et al., "Carbohydrate protection of enzyme structure and function against guanidinium chloride treatment depends on the nature of carbohydrate and enzyme," Eur. J. Biochem., 248:24-29, 1997.
Spiess et al., Trehalose is a potent PCR enhancer: Lowering of DNA melting temperature and thermal stabilization of Taq polymerase by the disaccharide trehalose. Clinical Chemistry, 50:1256-1259, 2004.
Stein and Moore, The free amino acids of human blood plasma. JCB, 211:915-926, 1954.
Stock et al., Effects of ionic liquids on the acetylcholinesterase—A structure-activity relationship consideration. Green Chemistry, 6:286-290, 2004.
Suslick et al., "Colorimetric sensor arrays for molecular recognition," Tetrahedron 60:11133-11138, 2004.
"The dose makes the poison." Yale chemsafe , (http://learn.caim.yale.edu/chemsafe/references/dose.html, downloaded Aug. 1, 2014, 1 page.
The Frontier energy solution, Inc.'s FAQ, http://www.frontierenergysolutionsinc.com/faq/, downloaded Jul. 31, 2014, 1 page.
Timasheff, "Water as Ligand: Preferential Binding and Exclusion of Denaturants in Protein Unfolding," Biochemistry, 3/(40:9857-9864, 1992.
U.S. Appl. No. 11/291,267 Office Action dated Jun. 13, 2014.
U.S. Appl. No. 12/182,926 Office Action dated Apr. 30, 2014.

(56) References Cited

OTHER PUBLICATIONS

U.S. Appl. No. 13/191,346 Office Action dated Jul. 22, 2014.
U.S. Appl. No. 11/102,588 Notice of Allowance dated Sep. 24, 2014.
U.S. Appl. No. 11/291,267 Office Action dated Mar. 12, 2015.
U.S. Appl. No. 12/509,303 Office Action dated Jun. 9, 2014.
U.S. Appl. No. 13/191,346 Office Action dated Jul. 2, 2015.
U.S. Appl. No. 13/191,346 Office Action dated Mar. 20, 2015.
U.S. Appl. No. 13/812,288 Office Action dated Aug. 25, 2016.
U.S. Appl. No. 13/812,288 Office Action dated Feb. 1, 2017.
U.S. Appl. No. 13/812,288 Office Action dated Feb. 11, 2016.
U.S. Appl. No. 13/812,288 Office Action dated Jan. 12, 2017.
U.S. Appl. No. 13/812,288 Office Action dated May 7, 2015.
U.S. Appl. No. 13/812,288 Restriction Requirement dated Oct. 9, 2014.
U.S. Appl. No. 13/966,117 Final Office Action dated Feb. 26, 2015.
U.S. Appl. No. 13/966,117 Office Action dated Sep. 25, 2014.
U.S. Appl. No. 14/895,475 Office Action dated Jan. 10, 2017.
U.S. Appl. No. 14/895,475 Office Action dated May 22, 2017.
Vanin, "Iron diethyldithiocarbamate as spin trap for nitric oxide detection," Meth. Enzymol., 301:269-79 (1999).
Voziyan et al., "Chaperonin-assisted folding of glutamine synthetase under nonpermissive conditions: Off-pathway aggregation propensity does not determine the co-chaperonin requirement," Protein Science, 9:2405-2412, 2000.
Wang et al., "A Naturally Occurring Protective System in Urea-Rich Cells: Mechanism of Osmolyte Protection of Proteins against Urea Denaturation," Biochemistry, 36:9101-9108, 1997.
Wang et al., "Antibody Structure, Instability, and Formulation," Journal of Pharmaceutical Sciences 96(1):1-26, 2007.
Wang et al., "Instability, stabilization, and formulation of liquid protein pharmaceuticals," International Journal of Pharmaceutics 185:129-188, 1999.
Wang, "Protein aggregation and its inhibition in biopharmaceutics," International Journal of Pharmaceutics 289:1-30, 2005.
Whitman et al., "Prokaryotes: the unseen majority," Proc. Natl. Acad. Sci. USA, 95:6578-83, 1998.
Whittlesey et al., "Delivery systems for small molecule drugs, proteins, and DNA: the neuroscience/biomaterial interface," Experimental Neurology 190:1-16, 2004.
Wierzbicka-Patynowski et al., "The ins and outs of fibronectin matrix assembly," Journal of Cell Science 116:3269-3276, 2003.
Yamamoto et al., "Molecular Design of Bioconjugated Cell Adhesion Peptide with a Water-Soluble Polymeric Modifier for Enhancement of Antimetastatic Effect," Current Drug Targets 3:123-130, 2002.
Yancey et al., "Living with Water Stress: Evolution of Osmolyte Systems," Science, 217:1214-1222, 1982.
Yang et al., Neuroprotection by 2-h postischemia administration of two free radical scavengers, alpha-phenyl-n-tert-butyl-nitrone (PBN) and N-tert-butyl-(2-sulfophenyl)-nitrone (S-PBN), in rats subjected to focal embolic cerebral ischemia., Exp. Neurol., 163(1):39-45, 2000.
Yoshida et al., Identification of the cis-Acting Endoplasmic Reticulum Stress Response Element Responsible for Transcriptional Induction of Mammalian Glucose-regulated Proteins: Involvement of basic leucine zipper transcription factors. J Biol Chem 273:33741-33749, 1998.
Zhao et al., "NXY-059, a novel free radical trapping compound, reduces cortical infarction after permanent focal cerebral ischemia in the rat," Brain Res., 909(1-2):46-50, 2001.
Zhi et al., "Renaturation of citrate synthase: Influence of denaturant and folding assistants," Protein Science, 1:522-529, 1992.
Extended EP Search Report, EP Patent Application No. 21188996.9, dated Jan. 5, 2022, 9 pages.

* cited by examiner

STABILIZATION OF THROMBOCYTES AT AMBIENT TEMPERATURES

CROSS-REFERENCE

This application is a continuation application of U.S. patent application Ser. No. 16/049,516, filed Jul. 30, 2018, which is a continuation application of U.S. patent application Ser. No. 15/316,677, filed Dec. 6, 2016, which is a U.S. National Phase Application of International Patent Application No. PCT/US2015/034967, filed Jun. 9, 2015, which claims the benefit of U.S. Provisional Application No. 62/010,151, filed Jun. 10, 2014, all of which are incorporated by reference herein in their entirety.

BACKGROUND OF THE INVENTION

1. Technical Field

The present invention relates generally to stabilization of one or more thrombocytes at ambient temperatures. In particular, the invention relates to formulations, compositions, articles of manufacture, kits and methods for substantially stable storage of one or more metabolically-active thrombocytes at ambient temperatures.

BACKGROUND

Whole blood is a complex mixture of cells, nucleic acids, proteins and various other analytes. In particular, blood components include, but are not limited to: cells, such as leukocytes (monocytes, lymphocytes and granulocytes), erythrocytes, thrombocytes and circulating tumor cells; nucleic acid molecules, such a circulating-free DNA (cfDNA); polypeptides, such as lipoproteins, albumin and serum proteins, and other various analytes.

Thrombocytes or platelets are anucleated cells that play a key role in the clotting of blood. Thrombocytes are small, disc-like cells that circulate in mammalian blood and are involved in hemostasis. Thrombocytes secrete a wide variety of growth factors that assist in promoting blood clotting and tissue regeneration.

The level of circulating thrombocytes in a healthy individual is controlled within a physiological range of about $(150\text{-}400) \times 10^3$ per $mm^3$. Suboptimal levels of thrombocytes (thrombocytopenia) can lead to excessive bleeding, whereas levels exceeding optimal concentrations can lead to the formation of thromboli (blood clots) that can obstruct blood vessels and can lead to higher risk of stroke, pulmonary embolus or myocardial infarction.

Circulating thrombocytes are typically present in an inactivated state, and are maintained in the inactivated state by factors produced by endothelial cells lining the blood vessel lumen. Upon disruption or injury to this endothelial layer, thrombocytes come in contact with collagen or von Wildebrand's factor, which activates the thrombocytes causing the thrombocytes to aggregate (i.e., clot). This activation and aggregation also may occur by the enzymatic activity of thrombin or in the presence of ADP. Upon activation, thrombocytes release the contents of alpha and dense granules that include growth factors and fibrinogen that assist in clot formation and help promote recruitment of fibroblasts to promote wound healing. Activated thrombocytes can be distinguished from inactivated thrombocytes by their more spherical/stellate shape.

The activation, aggregation and/or release of numerous growth factors and other intracellular components of thrombocytes during the collection of whole blood can greatly hinder the quantitation and analysis of these cells. The addition of various anti-coagulants to maintain an inactivated thrombocytes at ambient temperatures results in only about 13-52% inactivated thrombocytes at 24 hours making accurate quantitative analysis of total thrombocytes essentially impossible at this time point. Thus, there exists a need for improved formulations for and methods of stabilizing thrombocytes at ambient temperatures for a time sufficient for storage and shipping thrombocytes for research, diagnostic and therapeutic purposes.

SUMMARY OF THE INVENTION

The formulations, compositions and methods of the present invention advantageously provide for the stabilization of thrombocytes at ambient temperatures and these cells remain functional and retain the ability to be activated post-blood collection for a period of at least 24 hours, significantly increasing the time for storage and shipping of substantially stable thrombocytes for research, diagnostic and potential therapeutic applications. Disclosed herein in some embodiments, are formulations for substantially stable storage of one or more thrombocytes at ambient temperatures, wherein the one or more thrombocytes are stabilized for a period of at least six hours. In some embodiments, the one or more thrombocytes are stabilized in an inactivated state. In some embodiments, the one or more thrombocytes are in a blood sample. In some embodiments, the one or more thrombocytes are in an inactivated state in a blood sample. In some embodiments, the one or more thrombocytes are isolated from a blood sample. In some embodiments, at least 90% of the thrombocytes are stabilized in an inactivated state for a period of at least six hours. In some embodiments, at least 90% of the thrombocytes are stabilized in an inactivated state for a period of at least nine hours. In some embodiments, the thrombocytes are stabilized in an inactivated state for a period of at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours. In some embodiments, the formulation comprises: (i) a pH buffer; (ii) an anti-coagulant; (iii) at least one non-reducing sugar or polyol; and (iv) a functionalized carbohydrate. In some embodiments, the formulation comprises a polyol selected from the group consisting of glycol, glycerol, erythritol, threitol, arabitol, xylitol, ribitol, adonitol, mannitol, sorbitol, galactitol, fucitol, iditol and inositol, and combinations thereof. In some embodiments, the polyol is a pentose polyol or a hexose polyol. In some embodiments, the pentose polyol is adonitol. In some embodiments, the functionalized carbohydrate is sucralfate or sucrose octasulfate. In some embodiments, the functionalized carbohydrate is sucrose octasulfate. In some embodiments, the non-reducing sugar is sucrose or trehalose. In some embodiments, the non-reducing sugar is trehalose. In some embodiments, the anticoagulant is EDTA or hirudin. In some embodiments, the pH buffer is 2× phosphate buffered saline or Tris-HCl.

In one aspect of the invention, formulations are provided for substantially stable storage of one or more thrombocytes in an inactivated state in a blood sample at ambient temperatures, wherein the one or more thrombocytes are stabilized in an inactivated state for a period of at least six hours. In some embodiments, at least 90% of the thrombocytes are stabilized in an inactivated state for a period of at least six hours. In some embodiments, the thrombocytes are stabilized in an inactivated state for a period of at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours. In certain embodiments, the formulation comprises (i) a pH buffer, (ii) an anticoagulant, (iii) at least one non-reducing sugar or polyol, and (iv) a functionalized carbohydrate. In some embodiments, the polyol is selected from the group consisting of glycol, glycerol, erythritol, threitol, arabitol, xylitol, ribitol, adonitol, mannitol, sorbitol, galactitol, fucitol, iditol inositol, and combinations thereof. In some embodiments the polyol is a pentose polyol or a hexose polyol. In some embodiments, the polyol is adonitol. In some embodiments, the functionalized carbohydrate is sucralfate or sucrose octasulfate. In some embodiments, the functionalized carbohydrate is sucrose octasulfate. In some embodiments, the non-reducing sugar is sucrose or trehalose. In some embodiments, the non-reducing sugar is trehalose. In some embodiments, the anticoagulant is EDTA or hirudin. In some embodiments, the anticoagulant is EDTA, the functionalized carbohydrate is sucralfate or sucrose octasulfate, and the non-reducing sugar is sucrose or trehalose. In yet other embodiments, the anticoagulant is EDTA, the functionalized carbohydrate is sucrose octasulfate and the non-reducing sugar is trehalose. In some embodiments, the pH buffer is 2× phosphate buffered saline or Tris-HCl. Disclosed herein, in some embodiments are formulations for substantially stable storage of one or more thrombocytes at ambient temperatures, comprising a halogenated disaccharide derivative and an anticoagulant, wherein the one or more thrombocytes are stabilized for a period of at least six hours. In some embodiments, the one or more thrombocytes are stabilized in an inactivated state. In some embodiments, the one or more thrombocytes are in a blood sample. In some embodiments, the one or more thrombocytes are stabilized in an inactivated state in a blood sample. In some embodiments, the one or more thrombocytes are isolated from a blood sample. In some embodiments, the anticoagulant is hirudin. In some embodiments, the halogenated disaccharide derivative is selected from the group consisting of sucralose (1,6-dichloro-1,6-dideoxy-β-D-fructofuranosyl-4-chloro-4-deoxy-α-D-galactopyranoside), trichloronated maltose, 1,6-dichloro-1,6-dideoxy-β-D-fructofuranosyl-4-chloro-4-deoxy-6-O-monododecanoate-α-D-galactopyranoside, 1,6-sichloro-1,6-dideoxy-β-D-fructofuranosyl-4-chloro-4-deoxy-6-O-monotetradecanoate-α-D-galactopyranoside, and combinations thereof. In some embodiments, the formulation consists essentially of hirudin and sucralose (1,6-dichloro-1,6-dideoxy-β-D-fructofuranosyl-4-chloro-4-deoxy-α-D-galactopyranoside).

In some embodiments, there are provided formulations for substantially stable storage of one or more thrombocytes in an inactivated state in a blood sample at ambient temperatures, comprising a halogenated disaccharide derivative, wherein the one or more thrombocytes are stabilized in an inactivated state for a period of at least six hours. In some embodiments, the halogenated disaccharide derivative preferably is selected from the group consisting of sucralose (1,6-dichloro-1,6-dideoxy-β-D-fructofuranosyl-4-chloro-4-deoxy-α-D-galactopyranoside), trichloronated maltose, 1,6-dichloro-1,6-dideoxy-β-D-fructofuranosyl-4-chloro-4-deoxy-6-O-monododecanoate-α-D-galactopyranoside and 1,6-dichloro-1,6-dideoxy-β-D-fructofuranosyl-4-chloro-4-deoxy-6-O-monotetradecanoate-α-D-galactopyranoside, and more preferably the halogenated disaccharide derivative is sucralose (1,6-dichloro-1,6-dideoxy-β-D-fructofuranosyl-4-chloro-4-deoxy-α-D-galactopyranoside). In some embodiments, the formulations further comprise an anticoagulant, preferably hirudin. In some embodiments, the anticoagulant is hirudin. In some embodiments, the formulation consists essentially of hirudin and sucralose (1,6-dichloro-1,6-dideoxy-β-D-fructofuranosyl-4-chloro-4-deoxy-α-D-galactopyranoside).

Disclosed herein in some embodiments, are compositions of substantially, stably stored one or more thrombocytes comprising one or more thrombocytes admixed with a disclosed formulation. In some embodiments, the one or more thrombocytes are in a blood sample. In some embodiments, the one or more thrombocytes are isolated thrombocytes. In some embodiments, the one or thrombocytes are in an inactivated state.

Disclosed herein in some embodiments, are articles of manufacture, comprising a formulation described herein contained within a blood collection tube. In some embodiments, the blood collection tube is an evacuated blood collection tube.

Disclosed herein, in some embodiments, are kits comprising an article of manufacture described herein and a package insert.

Disclosed herein in some embodiments, are methods for substantially stable storage of one or more thrombocytes at ambient temperatures, comprising: admixing the one or more thrombocytes from a subject with a formulation provided herein, wherein the one or more thrombocyte is stabilized for a period of at least six hours. In some embodiments, the one or more thrombocytes are stabilized in an inactivated state. In some embodiments, the one or more thrombocytes are in a blood sample from the subject. In some embodiments, the one or more thrombocytes are stabilized in an inactivated state in a blood sample from the subject. In some embodiments, the one or more thrombocytes are isolated from a blood sample from the subject. In some embodiments, at least 90% of the thrombocytes are stabilized in an inactivated state for a period of at least six hours. In some embodiments, at least 90% of the thrombocytes are stabilized in an inactivated state for a period of at least nine hours. In some embodiments, the method further comprises activating the one or more thrombocyte in an inactivated state, by the addition of an activating agent to promote thrombocyte aggregation. In some embodiments, the activating agent is ADP. In some embodiments, the method further comprises activating the one or more thrombocyte by the addition of an activating agent to promote thrombocyte aggregation. In some embodiments, the activating agent is ADP. In some embodiments, the subject is an animal. In some embodiments, the subject is a mammal. In some embodiments, the mammal is a human.

Disclosed herein in some embodiments, are methods for substantially stable storage of one or more thrombocyte in an inactivated state in a blood sample at ambient temperatures, comprising, admixing a blood sample from a subject with a formulation provided herein, wherein the one or more thrombocytes are stabilized in an inactivated state for a period of at least six hours. In some embodiments, at least 90% of the thrombocytes are stabilized in an inactivated state for a period of at least six hours. In some embodiments, the thrombocytes are stabilized in an inactivated state for a period of at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours. In some embodiments, the blood sample is admixed with the stabilization formulation at the time the blood sample is collected from the subject to substantially stabilize the one or more thrombocytes in the inactivated state post collection from the subject. In some embodiments, the method further comprises activating the one or more thrombocytes by the additional of an activating agent. In some embodiments, the activating agent is ADP. In further embodiments of the methods, the subject is an animal, more preferably a mammal, and even more preferably a human.

DETAILED DESCRIPTION OF THE INVENTION

The present invention relates to formulations, compositions, articles of manufacture, kits, and methods for substantially stable storage of one or more thrombocyte at ambient temperatures. In some embodiments, the one or more thrombocytes are stored in an inactivated, but activatable, state in a blood sample. In one aspect, the formulations described herein beneficially maintain the integrity of inactivated, metabolically active, thrombocytes that may be subsequently analyzed for activation or that may be used in therapeutic applications for promoting blood clotting in a patient.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

"About" as used herein when referring to a measurable value such as an amount, a temporal duration, and the like, is meant to encompass variations of ±20% or ±10%, or ±5%, or even ±1% from the specified value, as such variations are appropriate for the disclosed compositions or to perform the disclosed methods.

Unless defined otherwise, all technical and scientific terms used herein have the same meaning as is commonly understood by one of skill in the art to which this invention belongs. All patents, patent applications and publications referred to herein are incorporated by reference in their entirety.

Formulations are provided, in some embodiments, for substantially stable storage of metabolically-active thrombocytes at ambient temperatures. In some embodiments, the thrombocytes are isolated from a blood sample. In some embodiments, the thrombocytes are in a blood sample. In some embodiments, the thrombocytes are inactivated. In certain embodiments, the thrombocyte stabilization formulations comprise a pH buffer, an anticoagulant, a non-reducing sugar, a polyol, and a functionalized carbohydrate. In certain other embodiments, the thrombocyte stabilization formulations comprise a pH buffer, an anticoagulant, a polyol and a functionalized carbohydrate. In certain other embodiments, the stabilization formulations comprise a pH buffer, an anticoagulant, a non-reducing sugar, and a functionalized carbohydrate. In still yet another embodiment, the stabilization formulations comprise a halogenated disaccharide derivative and an anticoagulant. In still yet another embodiment, the stabilization formulations comprise a halogenated disaccharide derivative, an anticoagulant, and a pH buffer. The formulations are capable of stabilizing at least 60%, 70%, 80% or even 90% inactivated, metabolically-active thrombocytes in a blood sample at ambient temperatures for a period of at least 6 hours, or at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours.

The term "ambient temperature" as used herein refers to common indoor room temperatures. In some embodiments, ambient temperature is 15 to 32° C. In some embodiments, ambient temperature is 20 to 27° C.

In another aspect of the present invention, formulations are provided for substantially stable storage of inactivated, metabolically-active thrombocytes in a blood sample at ambient temperatures. In certain embodiments, the thrombocyte stabilization formulations comprise a pH buffer, an anticoagulant, a non-reducing sugar, a polyol, and a functionalized carbohydrate. In certain other embodiments, the thrombocyte stabilization formulations comprise a pH buffer, an anticoagulant, a polyol, and a functionalized carbohydrate. In certain other embodiments, the stabilization formulations comprise a pH buffer, an anticoagulant, a non-reducing sugar, and a functionalized carbohydrate. In still yet another embodiment, the stabilization formulations comprise a halogenated disaccharide derivative and an anticoagulant. In still yet another embodiment, the stabilization formulations comprise a halogenated disaccharide derivative, an anticoagulant, and a pH buffer. The formulations are capable of stabilizing at least 60%, 70%, 80% or even 90% inactivated, metabolically-active thrombocytes in a blood sample at ambient temperatures for a period of at least 6 hours, or at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours.

In another aspect, compositions are provided herein in which a blood sample is admixed with a thrombocyte stabilization formulation to produce substantially stable one or more inactivated thrombocytes in a whole blood preparation. In still other embodiments, a composition comprising purified or substantially purified one or more thrombocyte admixed with a stabilization formulation of the present invention are provided.

Formulation Reagents

A. pH Buffers

According to certain embodiments, the herein described formulations and compositions for substantially stable storage of one or more thrombocytes include one or more pH buffers. In some embodiments, the pH buffer is any of a large number of compounds known in the art for their ability to resist changes in the pH of a solution, such as in an aqueous solution in which the pH buffer is present. Selection of one or more particular pH buffers for inclusion in a stable storage composition may be done based on the present disclosure and according to routine practices in the art, and may be influenced by a variety of factors including the pH that is desired to be maintained, the nature of the biological sample, the solvent conditions to be employed, the other components of the formulation to be used, and other criteria. For example, typically a pH buffer is employed at a pH that is within about 0.1, 0.2, 0.3, 0.4, 0.5, 0.6, 0.7, 0.8, 0.9 or 1.0 pH unit of a proton dissociation constant ($pK_a$) that is a characteristic of the buffer.

Non-limiting examples of pH buffers include citric acid, tartaric acid, malic acid, sulfosalicylic acid, sulfoisophthalic acid, oxalic acid, borate, CAPS (3-(cyclohexylamino)-1-propanesulfonic acid), CAPSO (3-(cyclohexylamino)-2-hydroxy-1-propanesulfonic acid), EPPS (4-(2-hydroxyethyl)-1-piperazinepropanesulfonic acid), HEPES (4-(2-hydroxyethyl)piperazine-1-ethanesulfonic acid), MES (2-(N-morpholino)ethanesulfonic acid), MOPS (3-(N-morpholino)propanesulfonic acid), MOPSO (3-morpholino-2-hydroxypropanesulfonic acid), PIPES (1,4-piperazinediethanesulfonic acid), TAPS (N-[tris(hydroxymethyl)methyl]-3-aminopropanesulfonic acid), TAPSO (2-hydroxy-3-[tris(hydroxymethyl)methylamino]-1-propanesulfonic acid), TES (N-[tris(hydroxymethyl)methyl]-2-aminoethanesulfonic acid), bicine (N,N-bis(2-hydroxyethyl)glycine), tricine (N-[tris(hydroxymethyl)methyl]glycine), tris (tris(hydroxymethyl)aminomethane) and bis-tris (2-[bis(2-hydroxyethyl)amino]-2-(hydroxymethyl)-1,3-propanediol). In some embodiments, including any of those set forth in Table 1, have a pH of about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0.

B. Polyols

Also as described herein, certain embodiments include at least one polyol in the composition for substantially stable storage of viable, inactivated thrombocytes in a whole blood sample at ambient temperatures. Polyols are polyhydric alcohols containing two or more hydroxyl groups and have the general formula $H(CHOH)_nH$, wherein n is an integer selected from 2 to 7 inclusive. Polyols differ in chain length with most polyols having five- or six carbon chains being derived from pentoses (five-carbon sugars) and hexoses (six-carbon sugars); however shorter and longer carbon chain polyols also exist. Exemplary polyols include, but are not limited to, glycol, glycerol, erythritol, threitol, arabitol, xylitol, ribitol, adonitol, mannitol, sorbitol, galactitol, fucitol, iditol and inositol. Selection of one or more particular polyols for inclusion in a substantially stable storage composition may be done based on the present disclosure and according to routine practices in the art, and may be influenced by a variety of factors including other formulation components. In certain embodiments, the polyol present in the formulation is a pentose polyol. In some embodiments, the polyol is adonitol. In some embodiments, the polyol is present at a concentration between 20-100 mM, or between about 25-75 mM. In some embodiments, the polyol is a pentose polyol and is present at a concentration between 20-100 mM, or between about 25-75 mM. In some embodiments, the polyol is adonitol and is present at a concentration between 20-100 mM, or between about 25-75 mM.

C. Disaccharide Derivatives

In certain embodiments, the formulations or compositions for substantially stable storage of one or more inactivated thrombocyte in a whole blood sample at ambient temperatures, including those in Table 1, include at least one halogenated disaccharide derivative. In some embodiments, the halogenated disaccharide derivative is a di- or tri-chlorinated disaccharide. In some embodiments, such di- or tri-chlorinated disaccharides unexpectedly are capable of substantially stable storage of inactivated thrombocytes either alone or in the presence of only a buffer. Halogenated disaccharide derivatives are known, e.g., see US Patent Publication No. 2014/0065062, and include sucralose (1,6-dichloro-1,6-dideoxy-β-D-fructofuranosyl-4-chloro-4-deoxy-α-D-galactopyranoside), trichloronated maltose, 1,6-dichloro-1,6-dideoxy-β-D-fructofuranosyl-4-chloro-4-deoxy-6-O-monododecanoate-α-D-galactopyranoside, and 1,6-dichloro-1,6-dideoxy-β-D-fructofuranosyl-4-chloro-4-deoxy-6-O-monotetradecanoate-α-D-galactopyranoside. Selection of one or more particular halogenated disaccharide derivative for inclusion in a substantially stable storage composition may be done based on the present disclosure and according to routine practices in the art, and may be influenced by a variety of factors including other formulation components. In some embodiments, the functionalized carbohydrate is sucralose and is present at about 1.0-50.0 mM. In some embodiments, the functionalized carbohydrate is sucralose and is present at about 10.0-30.0 mM. In some embodiments, the functionalized carbohydrate is sucralose and is present at about 25.0 mM.

D. Functionalized Carbohydrates

In some embodiments described herein, the formulations, including those in Table 1, include a functionalized carbohydrate. Exemplary functionalized carbohydrates include sucralfate or sucrose octasulfate and it will be appreciated that from the present disclosure the skilled person may select other functionalized carbohydrates for use in a stable storage formulations and compositions for viable, activatable, thrombocytes, as may vary based on the other components of the composition that are employed. In some embodiments, the concentration of functionalized carbohydrates in the present formulations and compositions, including those set forth in Table 1, is about 0.005-1.0 mM. In some embodiments, the concentration of functionalized carbohydrates in the present formulations and compositions, including those set forth in Table 1, is about 0.25-0.5 mM.

E. Non-Reducing Sugars

In some embodiments, the formulations and compositions for substantially stable storage of thrombocytes at ambient temperatures include at least one non-reducing sugar. In some embodiments, the formulations and compositions for substantially stable storage of viable, inactivated thrombocytes in a whole blood sample at ambient temperatures include at least one non-reducing sugar. As used herein, "non-reducing sugars" refers to carbohydrate molecules that lack a functional aldehyde group. Exemplary non-reducing sugars include sucrose and trehalose. In some embodiments, the non-reducing sugar is sucrose. In some embodiments, the non-reducing sugar is trehalose. In some embodiments, the trehalose is present at a concentration of about 1.0-50 mM. In some embodiments, the trehalose is present at a concentration of about 10.0-30 mM. In some embodiments, the trehalose is present at a concentration of about 25 mM.

F. Anticoagulants

In some embodiments, an anticoagulant is included in the presently described formulations or compositions. Such anticoagulants are known in the art. Exemplary anticoagulants include ethylenediaminetetraacetic acid (EDTA), hirudin, heparin, and sodium citrate. In some embodiments, the anticoagulant is hirudin. In some embodiments, the hirudin is present at a concentration of about 1.0-50 µg/mL. In some embodiments, the hirudin is present at a concentration of about 1.0-25 µg/mL. In some embodiments, the hirudin is present at a concentration of about 10-20 µg/mL.

Exemplary Formulations for Stabilization of Thrombocytes at Ambient Temperatures In some embodiments, the formulations, compositions and methods of the present invention advantageously provide for the substantially stable storage of thrombocytes at ambient temperatures for a period of at least six hours. In some embodiments, the formulations, compositions and methods of the present invention advantageously provide for the substantially stable storage of thrombocytes in their natural circulating, inactivated state in a blood sample at ambient temperatures, wherein the cells retain the ability to be activated post collection for a period of at least six hours. In other embodiments, at least 90% of the thrombocytes are stabilized in an inactivated state for a period of at least six hours. In other embodiments, the thrombocytes are stabilized in an inactivated state for a period of at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours.

In certain embodiments, the formulations for the substantially stable storage of thrombocytes at ambient temperatures comprise a pH buffer, an anticoagulant, a non-reducing sugar, a polyol, and a functionalized carbohydrate. In certain embodiments, the stabilization formulations comprise a pH buffer, an anticoagulant, a polyol, and a functionalized carbohydrate. In certain embodiments, the formulations for the substantially stable storage of thrombocytes comprise a pH buffer, an anticoagulant, a non-reducing sugar, and a functionalized carbohydrate. In some embodiments, the formulations for the substantially stable storage of thrombocytes comprise a halogenated disaccharide derivative, and an anticoagulant, and may further comprise a pH buffer. In some embodiments, the anti-coagulant is sprayed and dried on the blood collection tube, container, or vessel prior to collection of the blood sample from the subject. In some embodiments, the anti-coagulant is added directly to the formulations described herein.

In certain embodiments, the pH buffer is Tris-HCl, the polyol is a pentose alcohol, the non-reducing sugar is trehalose, the anticoagulant is EDTA or hirudin, and the functionalized carbohydrate is sucrose octasulfate. In certain embodiments, the pH buffer is Tris-HCl, the polyol is adonitol, the non-reducing sugar is the D+ isomer of trehalose, the anticoagulant is EDTA or hirudin, and the functionalized carbohydrate is sucrose octasulfate. In certain embodiments, the pH buffer is Tris-HCl, the polyol is adonitol, the non-reducing sugar is the D+ isomer of trehalose, the anticoagulant is hirudin, and the functionalized carbohydrate is sucrose octasulfate. In some embodiments, the disaccharide derivative is a halogenated disaccharide and the anticoagulant is hirudin. In some embodiments, the halogenated disaccharide is sucralose and the anticoagulant is hirudin.

In some embodiments, the formulations for the substantially stable storage of inactivated thrombocytes at ambient temperatures include the exemplary formulations provided in Table 1.

TABLE 1

Exemplary Formulations for Stabilizing Inactivated, Metabolically-active Thrombocytes in a Human Blood Sample at Ambient Temperatures

| Formulation | Tris-HCl (mM) | Adonitol (mM) | Trehalose (mM) | Sucrose Octasulfate (mM) | Sucralose (mM) |
|---|---|---|---|---|---|
| A | 2.5 | 100 |  | 1.0 |  |
| B | 2.5 | 50 | 25.0 | 1.0 |  |
| C | 2.5 |  | 25.0 | 1.0 |  |
| D | 2.5 | 50 | 25.0 | 0.5 |  |
| E | 2.5 |  |  |  | 25 |
| F |  |  |  |  | 25 |

Methods for Preparing Exemplary Formulations

In some embodiments, the exemplary Formulations A-F of Table 1 are prepared using materials commercially available from suppliers and preparing such formulations is accomplished using the methods disclosed herein as well as other methods known to those skilled in the art.

In some embodiments, pre-weighed solid components are added to a suitable vessel, such as a square bottle, to which the aqueous components are added. The reaction mixture is agitated, e.g., by shaking, until the solid components have completely dissolved and then the pH of the mixture is adjusted to the desired pH using a suitable acid, e.g., hydrochloric acid. The resulting formulations are then sterilized, e.g., using a 0.22 micron filter, and stored at room temperature.

In one example, a 50 mL preparation of a 20× Formula A is prepared as follows: 15.2034 gr of adonitol (Calbiochem, catalogue #121739) and 1.251 g sucrose octasulfate potassium salt (Toronto Research Chemicals, catalogue # S69900) are added to a square bottle. A 30 mL volume of water is added, followed by the addition of 2.5 mL of Tris-HCl (Invitrogen, catalogue #15567-027). Additional water is added to qc the formulation to a final total volume of 50 mL. The mixture is shaken until fully dissolved, and hydrochloric acid is added to adjust the pH to 7.51. The solution is sterile filtered (0.22 μm pore size) under vacuum to yield the resulting formulation.

In another example, a 50 mL preparation of a 20× Formula B is prepared as follows: 7.5994 g of adonitol, 9.4997 g D-(+)-trehalose dihydrate (Fluka, catalogue #90210), and 1.25 g sucrose octasulfate potassium salt are added to a square bottle. A 30 mL volume of water is added, followed by the addition of 2.5 mL of Tris-HCl (Invitrogen, catalogue #15567-027). Additional water is added to qc the formulation to a final total volume of 50 mL. The mixture is shaken until fully dissolved, and hydrochloric acid is added to adjust the pH to 7.51. The solution is sterile filtered (0.22 μm pore size) under vacuum to yield the resulting formulation.

In another example, a 50 mL preparation of a 20× Formula C is prepared as follows: 9.5003 g D-(+)-trehalose dehydrate and 1.2502 g sucrose octasulfate potassium salt are added to a square bottle. A 30 mL volume of water is added, followed by the addition of 2.5 mL of Tris-HCl (Invitrogen, catalogue #15567-027). Additional water is added to qc the formulation to a final total volume of 50 mL. The mixture is shaken until fully dissolved, and hydrochloric acid is added to adjust the pH to 7.52. The solution is sterile filtered (0.22 μm pore size) under vacuum to yield the resulting formulation.

In another example, a 50 mL preparation of a 20× Formula D is prepared as follows: 7.5994 g of adonitol, 9.5003 g D-(+)-trehalose dihydrate and 0.625 g sucrose octasulfate potassium salt. A 30 mL volume of water is added, followed by the addition of 2.5 mL of Tris-HCl (Invitrogen, catalogue #15567-027). Additional water is added to qc the formulation to a final total volume of 50 mL. The mixture is shaken until fully dissolved, and hydrochloric acid is added to adjust the pH to 7.51. The solution is sterile filtered (0.22 μm pore size) under vacuum to yield the resulting formulation.

In another example, a 50 mL preparation of a 20× Formula E is prepared as follows: 9.9997 g of sucralose (Sigma, catalogue #69293) is added to a square bottle. A 30 mL volume of water is added, followed by the addition of 2.5 mL of Tris-HCl (Invitrogen, catalogue #15567-027). Additional water is added to qc the formulation to a final total volume of 50 mL. The mixture is shaken until fully dissolved and hydrochloric acid is added to adjust the pH to 7.54. The solution is sterile filtered (0.22 µm pore size) under vacuum to yield the resulting formulation.

In another example, a 50 mL preparation of a 20× Formula F is prepared as follows: 9.9993 g of sucralose (Sigma, catalogue #69293) is added to a square bottle. Water is added to qc the formulation to a final total volume of 50 mL. The mixture is shaken until fully dissolved, providing a solution having a pH of 7.54. The solution is sterile filtered (0.22 µm pore size) under vacuum to yield the resulting formulation.

Purified Stabilized Thrombocytes

In some embodiments, the substantially stabilized one or more thrombocytes in a blood sample at ambient temperatures are purified using well known methods employed by those skilled in the art. Apparatus and kits for purifying thrombocytes from blood are well known (e.g., see U.S. Pat. Nos. 5,234,593; 6,315,706 and 7,708,152). In certain embodiments, the thrombocytes are purified using a bag PC (platelet concentrate) prepared after collection of blood in a bag and the apheresis PC obtained by the use of a component blood collecting device. These methods separate thrombocytes from blood using centrifugal separation. In some embodiments, substantially stabilized, intact, metabolically active viable cells are advantageously purified by affinity chromatography or by fluorescence activated cell sorting (FACS) analysis using antibodies generated against a native wild type membrane proteins and receptors, and which method is not possible using other storage formulations that denature these cellular proteins.

In some embodiments, the purified one or more thrombocyte are subsequently stored in the formulations described herein for extended periods before analysis or use.

Articles of Manufacture

In certain embodiments, articles of manufacture are provided, which comprise a formulation provided herein, contained within a suitable blood collection tube, container or vessel. In some embodiments, the formulation is selected from those set forth in Table 1. In some embodiments, these articles of manufacture are used for substantially stable storage of one or more blood component by stabilizing one or more blood component at the time of blood collection. In certain embodiments, the blood collection tube is an evacuated blood tube having less than atmospheric pressure to withdraw a predetermined volume of whole blood. In some embodiments, these articles of manufacture are used in the kits and methods described herein.

Kits

In certain embodiments, there are provided kits comprising any one of the articles of manufacture described herein and a package insert. In some embodiments, the components of the kit are supplied in a packaging means, such as a compartmentalized plastic enclosure, preferably with a hermetically sealable cover so that the contents of the kit can be sterilized and sealed for storage.

Methods for Substantially Stable Storage of One or More Thrombocyte in a Blood Sample at Ambient Temperatures Described herein, in some embodiments, are methods for substantially stable storage of one or more thrombocyte at ambient temperatures. In some embodiments, the methods are for substantially stable storage of one or more thrombocytes in an inactivated state in a blood sample at ambient temperatures.

In certain embodiments, the methods comprise admixing a blood sample with a formulation for substantially stable storage of one or more thrombocyte at ambient temperatures for a period of at least six hours. In some embodiments, the one or more thrombocytes are isolated from a blood sample. In some embodiments, the one or more thrombocytes are stabilized in an inactivated state. In some embodiments, at least 90% of the thrombocytes remain in an inactivated state for a period of at least six hours. In other embodiments, the thrombocytes are stabilized in an inactivated state for a period of at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours. In certain embodiments, the formulation is one of the formulations set forth in Table 1.

In certain embodiments, the methods comprise admixing a blood sample with a formulation for substantially stable storage of viable thrombocytes, wherein the formulation comprises a pH buffer, an anticoagulant, a non-reducing sugar, a polyol and a functionalized carbohydrate. In certain embodiments, the thrombocyte stabilization formulations comprise a pH buffer, an anticoagulant, a polyol, and a functionalized carbohydrate. In certain embodiments, the stabilization formulation comprises a pH buffer, an anticoagulant, a non-reducing sugar, and a functionalized carbohydrate. In still yet another embodiment, the stabilization formulation comprises a halogenated disaccharide derivative and an anticoagulant. In still yet another embodiment, the stabilization formulation comprises a halogenated disaccharide derivative and an anticoagulant furthers comprise a pH buffer. In certain embodiments, the formulation is one of the formulations set forth in Table 1.

In certain embodiments, the methods comprise admixing a blood sample with a formulation for substantially stable storage of viable, activatable thrombocytes in a blood sample, wherein the formulation comprises a pH buffer, an anticoagulant, a non-reducing sugar, a polyol, and a functionalized carbohydrate. In certain embodiments, the thrombocyte stabilization formulation comprises a pH buffer, an anticoagulant, polyol, and a functionalized carbohydrate. In certain other embodiments, the stabilization formulation comprises a pH buffer, an anticoagulant, a non-reducing sugar, and a functionalized carbohydrate. In still yet another embodiment, the stabilization formulation comprises a halogenated disaccharide derivative and an anticoagulant. In still yet another embodiment, the stabilization formulation further comprises a pH buffer. In certain embodiments, the formulation is one of the formulations set forth in Table 1.

Blood collection tubes, bags, containers and vessels are well-known in the art and have been employed by medical practitioners for decades. Blood collected for substantially stable storage of one or more blood component may be obtained from a subject, donor, or patient using any method or apparatus commonly employed by those skilled in the art such as venipuncture or finger prick. In some embodiments, when the blood is collected by venipuncture, a formulation described herein is located inside the blood collection tube, e.g., an evacuated tube (Vacutainer, Becton Dickenson or Vacuette, Greiner) at the time that the blood sample is obtained from the donor or patient. In some embodiments, the stabilization formulation is added to an already obtained whole blood sample, preferably immediately or shortly after it is withdrawn.

In some embodiments, the methods described herein use the articles of manufacture and kits disclosed.

The following Examples are presented by way of illustration and not limitation.

Example 1: Stabilization of Inactive Thrombocytes in a Human Blood Sample for a Period of at Least 22 Hours at Ambient Temperature This Example describes formulations of the present invention for stabilizing inactivated thrombocytes that remain capable of being activated after being stored for a period of 22 hours at ambient temperatures.

Whole blood samples were collected from six human donors using commercially available hirudin-coated collection tubes (Roche Diagnostics), the blood samples were pooled and within three hours of collection, blood samples were processed. A 300 µL aliquot of each whole blood sample was transferred to an Eppendorf tube at a 1:20 ratio with 15 µL of stabilizer formulation A, B, C, or D of Table 1, either prior to or following the addition of the stabilizer formulation, and the mixtures were kept at ambient temperatures for predetermined time periods before being analyzed. An equal volume of whole blood was added to each control sample, and each sample was stored at room temperature in the absence of the stabilizer formulation and processed in parallel with the test samples.

To 300 µL of each mixture and control, 300 µL of NaCl 0.9% and 20 µL of the provided ADP solution was added to promote activation of the thrombocytes and the samples were analyzed using a multiplate analyzer (Roche Diagnostics). Thrombocyte activity in each condition was measured immediately after sample set-up (Time 0) using the multiplate analyzer and ADP test according to the manufacturer's instructions. Thrombocyte activity was also measured at 3 hour, 6 hour, 9 hour and 22 hour time points. Thrombocyte activity in each condition was normalized to its Time 0 measurement. Data from the six donors were then averaged. The data are shown in Table 2.

TABLE 2

Stabilization of Viable, Activatable Thrombocytes in a Human Blood Sample for at Least 22 Hours

| Time (hr) | Control | Formulation A | Formulation B | Formulation C | Formulation D |
| --- | --- | --- | --- | --- | --- |
| 0 | 100* | 100 | 100 | 100 | 100 |
| 3 | 93 | 110 | 112 | 96 | 98 |
| 6 | 82 | 107 | 111 | 101 | 95 |
| 9 | 77 | 115 | 114 | 101 | 93 |
| 22 | 59 | 91 | 92 | 74 | 90 |

*Values are shown as present activity remaining relative to Time 0

As shown in Table 2, after the 9 hour incubation period, the mean decrease in thrombocyte activity in the NF control condition was −23% compared with +15%, +14%, +1% and −7% for Formulations A, B, C, and D of Table 2, respectively. After a 22 hour incubation period, significant thrombocyte activity was still detected with a mean decrease in thrombocyte activity in the NF control condition of −41%, compared with −9%, −8%, −26% and −10% for Formulations A, B, C, and D of Table 2, respectively.

Formulations of Table 1 comprising a halogenated disaccharide derivative, sucralose, were characterized as described above, and also were identified as possessing stabilizing thrombocyte activity in whole blood for at least 22 hours (Table 3). In this study, these formulations, as set forth in Table 1, were incorporated into hirudin vacuum blood collection tubes prior to blood draw.

TABLE 3

Stabilization of Viable, Activatable Thromobocytes in a Human Blood Sample for at Least 22 Hours

| Formulation | Time 0 | 3 Hours | 6 Hours | 9 Hours | 22 Hours |
| --- | --- | --- | --- | --- | --- |
| Control | 100 | 89 | 69 | 58 | 60 |
| E | 100 | 100 | 99 | 98 | 97 |
| F | 100 | 94 | 87 | 80 | 73 |

* Values are shown as present activity remaining relative to Time 0

During room temperature blood incubation, thrombocyte activity in the NF control condition decreased by −40% by the 22 hour time point, compared with −3% for Formula E and −27% for Formula F of Table 1.

Unless the context requires otherwise, throughout the present specification and claims, the word "comprise" and variations thereof, such as, "comprises" and "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A composition for stabilizing at least one component of a blood sample at ambient temperatures, the composition comprising:
(i) a pH buffer;
(ii) a halogenated disaccharide derivative; and
(iii) a polyol.

2. The composition of claim 1, wherein the pH buffer comprises Tris-HCl, citric acid, or 2X phosphate buffered saline.

3. The composition of claim 1, wherein the pH of the composition is in the range of about 4.0 to about 9.0.

4. The composition of claim 1, wherein the halogenated disaccharide derivative is a di- or tri-chlorinated disaccharide.

5. The composition of claim 1, wherein the halogenated disaccharide derivative is sucralose (1,6-dichloro-1,6-dideoxy-β-D-fructofuranosyl-4-chloro-4-deoxy-α-D-galactopyranoside); trichloronated maltose; 1,6-dichloro-1,6-dideoxy-β-D-fructofuranosyl-4-chloro-4-deoxy-6-O-monododecanoate-α-D-galactopyranoside; 1,6-dichloro-1,6-dideoxy-β-D-fructofuranosyl-4-chloro-4-deoxy-6-O-monotetradecanoate-α-D-galactopyranoside; or any combinations thereof.

6. The composition of claim 1, wherein the polyol is selected from the group consisting of glycol, glycerol, erythritol, threitol, arabitol, xylitol, ribitol, adonitol, mannitol, sorbitol, galactitol, fucitol, iditol, and inositol, or any combinations thereof.

7. The composition of claim 1, wherein the polyol is present at a concentration ranging from about 90 mM to about 2.5 M.

8. The composition of claim 1, wherein the composition further comprises at least one of a functionalized carbohydrate, a non-reducing sugar, and/or an anticoagulant.

9. The composition of claim 8, wherein the functionalized carbohydrate is sucralfate, sucrose octasulfate, or a combination thereof.

10. The composition of claim 8, wherein the non-reducing sugar is sucrose, trehalose, or a combination thereof.

11. The composition of claim 8, wherein the anticoagulant is selected from the group consisting of ethylenediaminetetraacetic acid (EDTA), hirudin, heparin, and sodium citrate, or any combination thereof.

12. A blood collection tube comprising the composition of claim 1.

13. A method for stabilizing at least one component of a blood sample at ambient temperatures, the method comprising:
admixing a blood sample from a subject with a composition to form a mixture, the composition comprising:
(i) a pH buffer;
(ii) a halogenated disaccharide derivative; and
(iii) a polyol; and
storing the mixture at ambient temperatures for at least six hours.

14. The method of claim 13, wherein the pH buffer comprises Tris-HCl, citric acid, or 2X phosphate buffered saline.

15. The method of claim 13, wherein the polyol is selected from the group consisting of glycol, glycerol, erythritol, threitol, arabitol, xylitol, ribitol, adonitol, mannitol, sorbitol, galactitol, fucitol, iditol, and inositol, or any combinations thereof.

16. The method of claim 13, wherein the composition further comprises at least one of a functionalized carbohydrate, a non-reducing sugar, and/or an anticoagulant.

17. The method of claim 13, wherein the at least one component of a blood sample is one or more of a cell, a nucleic acid molecule, a peptide or polypeptide, or any combination thereof.

* * * * *